United States Patent
Stevens et al.

(10) Patent No.: US 11,605,469 B2
(45) Date of Patent: Mar. 14, 2023

(54) COGNITIVE ANALYSIS OF DATA USING GRANULAR REVIEW OF DOCUMENTS

(71) Applicant: International Business Machines Corporation, Armonk, NY (US)

(72) Inventors: Richard J Stevens, Monkton, VT (US); Fernando Jose Suarez Saiz, Armonk, NY (US); Adam Clark, Mantorville, MN (US)

(73) Assignee: International Business Machines Corporation, Armonk, NY (US)

( * ) Notice: Subject to any disclaimer, the term of this patent is extended or adjusted under 35 U.S.C. 154(b) by 1126 days.

(21) Appl. No.: 16/218,692

(22) Filed: Dec. 13, 2018

(65) Prior Publication Data

US 2020/0194131 A1 Jun. 18, 2020

(51) Int. Cl.
*G16H 70/00* (2018.01)
*G16H 70/40* (2018.01)
*G16H 50/70* (2018.01)
*G06N 5/022* (2023.01)
*G06V 30/418* (2022.01)

(52) U.S. Cl.
CPC ............ *G16H 70/40* (2018.01); *G06N 5/022* (2013.01); *G06V 30/418* (2022.01); *G16H 50/70* (2018.01)

(58) Field of Classification Search
CPC ........ G16H 70/40; G16H 50/70; G06N 5/022; G06V 30/418
See application file for complete search history.

(56) References Cited

U.S. PATENT DOCUMENTS

| | | | | |
|---|---|---|---|---|
| 6,584,445 | B2 * | 6/2003 | Papageorge | G16H 15/00 434/226 |
| 7,809,660 | B2 * | 10/2010 | Friedlander | G16H 10/60 706/45 |
| 8,706,519 | B2 | 4/2014 | Gliklich | |
| 10,691,774 | B2 * | 6/2020 | Thorpe | G16H 70/00 |
| 2004/0044547 | A1 * | 3/2004 | Klennert | G16H 10/20 705/2 |
| 2012/0016690 | A1 * | 1/2012 | Ramarajan | G16H 50/20 705/2 |
| 2012/0047105 | A1 * | 2/2012 | Saigal | G16Z 99/00 706/54 |
| 2013/0035956 | A1 * | 2/2013 | Carmeli | G06Q 10/10 705/3 |

(Continued)

*Primary Examiner* — William L Bashore
*Assistant Examiner* — David Faber
(74) *Attorney, Agent, or Firm* — Patterson + Sheridan, LLP

(57) ABSTRACT

Techniques for granular analysis of a knowledge graph are provided. A profile comprising a plurality of attributes is received, and a knowledge graph is analyzed to identify a plurality of therapies, based on the plurality of attributes. A document that is relevant to a first therapy of the plurality of therapies is identified, and a criterion stated in the document is determined. Further, an aggregate value is determined for the criterion, based on a plurality of participants associated with the document, wherein the first aggregate value represents attributes of the plurality of participants. A weight is generated for the document, based at least in part on the plurality of attributes and the aggregate value. A score is generated for the first therapy, based at least in part on the weight, and an optimal therapy is determined, from the plurality of therapies, based in part on the score.

17 Claims, 12 Drawing Sheets

(56) References Cited

U.S. PATENT DOCUMENTS

| | | | |
|---|---|---|---|
| 2013/0041683 A1* | 2/2013 | Boissel | G16B 40/20 705/2 |
| 2014/0122113 A1* | 5/2014 | Hoffman, Jr. | G16H 10/20 705/2 |
| 2014/0316793 A1* | 10/2014 | Pruit | G16H 10/20 705/2 |
| 2016/0015493 A1* | 1/2016 | Ertl | A61B 34/20 433/215 |
| 2016/0154937 A1* | 6/2016 | Hennenfent | G06Q 10/0639 705/2 |
| 2016/0188813 A1* | 6/2016 | Hennenfent | G16H 40/20 705/2 |
| 2017/0076046 A1 | 3/2017 | Barnes et al. | |
| 2017/0277841 A1* | 9/2017 | Shankar | G16Z 99/00 |
| 2017/0351830 A1* | 12/2017 | Burger | G16H 80/00 |
| 2018/0181718 A1* | 6/2018 | Zaher | G16H 70/20 |
| 2019/0108315 A1* | 4/2019 | Thornton | G16H 10/60 |
| 2019/0252074 A1* | 8/2019 | Datla | G06F 17/10 |
| 2020/0167664 A1* | 5/2020 | Stevens | G06N 5/02 |
| 2020/0185098 A1* | 6/2020 | Stevens | G06N 5/022 |
| 2020/0234801 A1* | 7/2020 | Mao | G16H 10/20 |
| 2020/0342970 A1* | 10/2020 | Thorpe | G16H 70/40 |
| 2021/0407694 A1* | 12/2021 | Deckert | G16H 15/00 |

\* cited by examiner

COGNITIVE ANALYSIS OF DATA USING GRANULAR REVIEW OF DOCUMENTS

BACKGROUND

The present disclosure relates to cognitive analysis of data, and more specifically, to parsing and analyzing knowledge graphs based on a granular understanding of the underlying documentation.

In a variety of domains, studies, experiments, and trials are performed to understand how potential options or selections interact and compare to each other. For example, in the medical field, studies and trials are performed to determine the efficacy of new and existing therapies, in order to determine the best practices for treating or curing illnesses or disorders. Frequently, the results of these studies, experiments, and trials are published for review by others. Currently, the published literature is reviewed manually by subject-matter experts (SMEs) to determine the state of the field, and provide guidance with respect to optimal therapies. However, these determinations are time-consuming, expensive, and inherently biased. Further, the published literature is expanding at an increasing and unprecedented rate. As the number of published documents increases, it has become impossible to aggregate and interpret them all. Thus, current guidelines and best practices are universally outdated, and potentially conflict with newly discovered therapies or interactions.

Additionally, when patients are to be treated, healthcare providers determine the relevancy or value of different studies and therapies based on the cohort of the patient, and the disorder to be treated. Generally, the relevancy of a document is based on criteria stated in the document (e.g., which cohort the results apply to). This approach is insufficiently granular, and can lead to broader conclusions and generalizations than are appropriate, given the published literature. Further, given the rapid pace and complexity of the published literature, it is impossible for healthcare providers to identify and evaluate the potential therapies and the relevancy of each document. Thus, patient outcomes are often worse than they could be.

SUMMARY

According to one embodiment of the present disclosure, a method is provided. The method includes receiving a first profile comprising a first plurality of attributes, and analyzing a knowledge graph to identify a plurality of therapies, based on the first plurality of attributes. The method further includes identifying a first document that is relevant to a first therapy of the plurality of therapies. Additionally, the method includes determining a first criterion stated in the first document, and determining a first aggregate value for the first criterion, based on a plurality of participants associated with the first document, wherein the first aggregate value represents attributes of the plurality of participants. The method also includes generating a first weight for the first document, based at least in part on the first plurality of attributes and the first aggregate value. Finally, the method includes generating a first score for the first therapy, based at least in part on the first weight, and determining an optimal therapy, from the plurality of therapies, based in part on the first score.

According to a second embodiment of the present disclosure, a computer-readable storage medium is provided. The computer-readable storage medium has computer-readable program code embodied therewith, which is executable by one or more computer processors to perform an operation. The operation includes receiving a first profile comprising a first plurality of attributes, and analyzing a knowledge graph to identify a plurality of therapies, based on the first plurality of attributes. The operation further includes identifying a first document that is relevant to a first therapy of the plurality of therapies. Additionally, the operation includes determining a first criterion stated in the first document, and determining a first aggregate value for the first criterion, based on a plurality of participants associated with the first document, wherein the first aggregate value represents attributes of the plurality of participants. The operation also includes generating a first weight for the first document, based at least in part on the first plurality of attributes and the first aggregate value. Finally, the operation includes generating a first score for the first therapy, based at least in part on the first weight, and determining an optimal therapy, from the plurality of therapies, based in part on the first score.

According to a third embodiment of the present disclosure, a system is provided. The system includes one or more computer processors, and a memory containing a program which when executed by the one or more computer processors performs an operation. The operation includes receiving a first profile comprising a first plurality of attributes, and analyzing a knowledge graph to identify a plurality of therapies, based on the first plurality of attributes. The operation further includes identifying a first document that is relevant to a first therapy of the plurality of therapies. Additionally, the operation includes determining a first criterion stated in the first document, and determining a first aggregate value for the first criterion, based on a plurality of participants associated with the first document, wherein the first aggregate value represents attributes of the plurality of participants. The operation also includes generating a first weight for the first document, based at least in part on the first plurality of attributes and the first aggregate value. Finally, the operation includes generating a first score for the first therapy, based at least in part on the first weight, and determining an optimal therapy, from the plurality of therapies, based in part on the first score.

DETAILED DESCRIPTION

Figure 1:
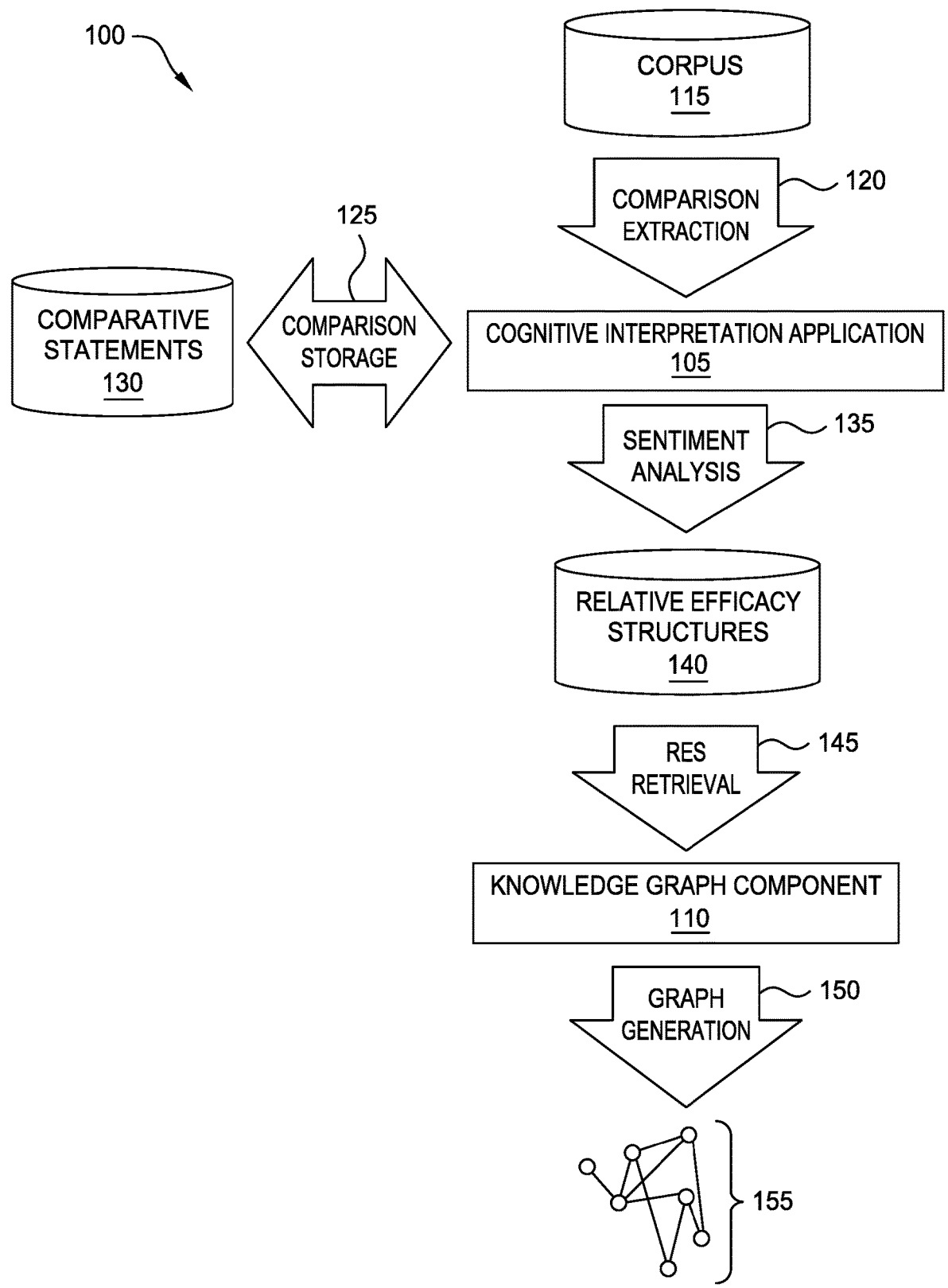
FIG. 1 illustrates a workflow for cognitively determining the relative efficacy of therapies, according to one embodiment disclosed herein.

In embodiments of the present disclosure, therapies are identified and evaluated for patients based on information contained in a knowledge graph. In some embodiments, a set of defined or accepted treatments or therapies are identified for a given patient or cohort. In an embodiment, these therapies are represented in a knowledge graph that is constructed based on published literature to enable comparisons to be drawn between the options. In one embodiment, the therapies are evaluated to determine relative efficacies and expected outcomes for patients in the cohort. In one embodiment, the relative efficacies of the therapies are determined with respect to individual cohorts of patients. For example, a given study or trial may indicate that with respect to a first cohort, outcomes improved. Typically, the indicated cohort refers to the stated criteria used when enrolling patients in the study. For example, the study criteria may request non-smoking patients that are under 65 and do not have hypertension.

In one embodiment, if the index patient (e.g., the patient to be treated) aligns with the stated criteria (such that they could have enrolled in the trial), the document is considered when determining the best therapy for the patient. In some embodiments, a document can be considered (with a reduced weight) if the index patient matches some, but not all, of the criteria. Further, in some embodiments of the present disclosure, a more granular approach is utilized to analyze the actual attributes of the individuals in the study, rather than simply the stated criteria. That is, in one embodiment, the documents are weighted based on how closely the index patient's attributes align with the actual participants, and not merely based on how closely the index patient aligns with the stated criteria, as discussed in more detail below. For example, in such an embodiment, suppose a study criterion requires participants be younger than 65. If the average age of participants in the study was 58, but the index patient is 22, the weight of the trial can be reduced, based on determining that the index patient differs from the actual patients under study (despite the fact that the index patient satisfies the trial criteria).

Further, in one embodiment, the attributes of the actual participants are analyzed to determine whether there are one or more shared attributes that are not reflected in the stated criteria. If so, the score or weight of the trial or document can be adjusted based on whether the attributes of the index patient aligns with these shared attributes. For example, suppose the study criteria specify that participants should be non-hypertensive males between 18 and 35. Suppose further that it is determined that most (or all) of the participants do not consume tobacco or alcohol (although tobacco and alcohol use are not listed in the stated criteria). In an embodiment, the weight of the study can be adjusted (e.g., increased or decreased) based on whether the index patient consumes tobacco and/or alcohol.

In this way, patient outcomes are improved because therapies are evaluated and scored based on a more granular analysis of the underlying data. Based on these evaluations, the healthcare provider can make more informed decisions about up-to-date therapies and comparisons based on a knowledge graph that takes into account new literature as it is produced. In an embodiment, before potential therapies can be identified, a knowledge graph must be constructed. In some embodiments, the knowledge graph is generated based on comparative statements (e.g., comparisons between therapies) found in published literature. In one embodiment, the knowledge graph is also built based on non-comparative statements (e.g., statements about the efficacy or outcomes of particular therapies, without any explicit comparison to other therapies).

In some embodiments of the present disclosure, techniques for cognitive analysis, representation, and interpretation of published literature are provided. In one embodiment, a corpus of medical literature is parsed and analyzed to identify and extract comparative statements or opinions made by the authors of the paper. For example, in a conclusion or summary, the authors may indicate that a particular therapy showed improved results, as compared to one or more other therapies (or as compared to the known or popular literature and practices). These conclusions are provided in natural language text, and are rarely structured in a way that allows for easy ingestion of the information. Embodiments of the present disclosure are discussed with reference to medical literature. However, these examples are not limiting on the present disclosure, and one of skill in the art will recognize other domains and literature that the present embodiments can be applied to.

In one embodiment, these comparative statements are interpreted to determine a sentiment of the statement, and the relative efficacy of each therapy discussed. In some embodiments, a data structure, referred to herein as a relative efficacy structure or RES, is generated to capture the natural language comparative statement in a useful format. For example, in one embodiment, the RES has a number of dimensions, including the directionality of the comparison (e.g., which therapy is superior), the magnitude of the difference, the particular outcome the statement refers to (e.g., survival, progression-free survival, remission, etc.), qualifiers of the statement (e.g., limitations or specifications), and the like. In an embodiment, each RES is also associated with a weight, which is based on a variety of factors related to the underlying comparative statement and the nature of the article it is contained in.

In one embodiment, if a comparison is found in one direction (e.g., that treatment A is better than treatment B), a complementary RES is created in the opposite direction (e.g., indicating that treatment B is worse than treatment A). In this way, queries for information for a given treatment or therapy can identify all documents that involve the therapy, regardless of whether the document deemed the therapy to be superior or inferior.

In some embodiments, a knowledge graph can be generated based on the determined relationships extracted from one or more published document. For example, in one embodiment, each node in the knowledge graph corresponds to a particular therapy, and each edge corresponds to one or more RESs. In this way, the knowledge graph can be interrogated or searched to identify optimal treatment options for a given patient, based on a tremendous variety of medical literature. In such an embodiment, patient outcomes are improved, as the current state of the literature can be captured and ingested into the knowledge graph rapidly, reducing or eliminating the need for SME review. Further, in embodiments, the RESs provide additional insight and knowledge that is not accessible or present in existing solutions. Thus, embodiments of the present disclosure enable high-precision searching, and allow users to analyze the literature at a more granular level.

In some embodiments, users can search or query the knowledge graph based on therapies, cohorts, disorders, and the like, to return a subset of the graph that is relevant to the search. Further, in some embodiments, nodes and/or connections can be selected to retrieve a link to any documents or published literature that was analyzed to create the node or edge. In this way, users can readily access the relevant literature, if they wish to investigate further or obtain more information about why the topology of the graph is shaped as it is, as well as why particular connections exist.

Embodiments of the present disclosure can be applied to extract and interpret comparative statements made in any field. In one embodiment, medical literature (e.g., published studies, trials, experiments, and the like) is ingested. In some embodiments, the literature is analyzed to identify comparisons or statements about relative efficacy between therapy options. In an embodiment, a therapy is any treatment used to treat a disorder. As used herein, therapies can include drugs, medications, exercises, surgeries, use of equipment, prescribed activities, and the like. Further, in embodiments, therapies can include refraining from certain activities and withdrawing or reducing treatments. Additionally, in embodiments, a therapy may include multiple treatments or prescribed activities (e.g., multiple medications). As used herein, a medical disorder can include any illness or medical condition, including but not limited to mental or physical disease, sickness, disability, infection, symptoms, conditions, or statuses.

FIG. 1 illustrates a workflow 100 for cognitively determining the relative efficacy of therapies, according to one embodiment disclosed herein. In the illustrated embodiment, a Cognitive Interpretation Application 105 analyzes documents to extract Comparative Statements 130 and generate RESs 140, and a Knowledge Graph Component 110 analyzes these RESs 140 to generate a Knowledge Graph 155. In some embodiments, a Knowledge Graph 155 is generated to aid visualization or understanding of the literature (although it may not actually be displayed). In some embodiments, however, the knowledge graph is not created, and the RESs 140 are used for other purposes. That is, in some embodiments, the generated RESs are usable or searchable by other systems or components, and can be utilized to aid understanding and improve treatment selection, without the construction of a knowledge graph.

In the illustrated workflow 100, the Cognitive Interpretation Application 105 analyzes a Corpus 115 of documents to perform Comparison Extraction 120. In an embodiment, the Corpus 115 includes documents which include at least some portion of natural language text, which may or may not have comparative statements by the author(s). In some embodiments, the Corpus 115 corresponds to a particular domain of interest to a user. For example, in one embodiment, a larger corpus or collection of documents is searched to identify a subset of the documents that relate to a particular disorder, therapy, or set of disorders or therapies. In such an embodiment, this subset of documents makes up the Corpus 115. In some embodiments, the workflow 100 is performed on multiple corpora (e.g., once for each therapy or disorder).

In an embodiment, the Comparison Extraction 120 comprises utilizing one or more natural language processing (NLP) techniques to identify comparative statements in the text included in the Corpus 115. For example, in one embodiment, the Cognitive Interpretation Application 105 searches for comparative language (such as "superior," "better," "worse," "improved," and the like). In some embodiments, the Cognitive Interpretation Application 105 analyzes predefined sections of the documents to identify these comparative statements (e.g., the abstract, conclusion, methods, discussion, etc.). That is, in an embodiment, a user or administrator can specify portions or sections in the documents that should be analyzed. In other embodiments, the Cognitive Interpretation Application 105 analyzes the full text of the document. In one embodiment, the Cognitive Interpretation Application 105 first searches the identified sections (as identified by their headings or by metadata tags), and only parses the rest of the document if the specified section(s) do not include any comparative statements (or if the specified section(s) cannot be found or do not exist in the document).

In some embodiments, the Comparison Extraction 120 also includes remedying unknown terms in the statement, such as through disambiguation and acronym resolution. For example, if the comparative statement includes an acronym, in one embodiment, the Cognitive Interpretation Application 105 can expand the acronym. Similarly, if the statement includes ambiguous or general language (such as, "all treatments studied herein", "with respect to the relevant cohort," or "generic chemotherapy drugs"), the Cognitive Interpretation Application 105 can determine a meaning for the terms. In some embodiments, the Cognitive Interpretation Application 105 first parses the selected document to identify the meaning of the term. That is, the Cognitive Interpretation Application 105 attempts to find meaning for the unknown term by analyzing the text of the document in which the comparative statement was found using NLP techniques. If no satisfactory disambiguation is found (e.g., the confidence level of any potential disambiguations is below a threshold), the Cognitive Interpretation Application 105 can access other literature (or one or more knowledge graphs) to disambiguate the term. In some embodiments, if the true meaning is not found within the corresponding document, the confidence or weight of the extracted comparison is reduced.

In some embodiments, Comparison Extraction 120 includes annotation of the extracted comparative statements. For example, in one embodiment, the Cognitive Interpretation Application 105 utilizes one or more NLP techniques to identify the therapy or therapies involved in the statement, the qualifier or comparative term utilized, and the like. In some embodiments, the Cognitive Interpretation Application 105 also determines the cohort(s) to which the statement(s) apply, as discussed in more detail below. Additionally, in some embodiments, the Cognitive Interpretation Application 105 determines characteristics of the comparative statements, such as where in the text it was located (e.g., which section it was found in), the publication date of the document, whether the document has been peer-reviewed, an identity of the publisher or entity that provided the document, and the like.

In the illustrated embodiment, the Cognitive Interpretation Application 105 stores the extracted comparisons (e.g., the natural language text) in a data store for Comparative Statements 130 (as indicated by Comparison Storage 125). In some embodiments, these stored Comparative Statements 130 are annotated to identify the relevant therapies, qualifiers, and the like. In some embodiments, the Comparative Statements 130 also indicate the disorder that is relevant to the comparison. In other embodiments, the disorder is described by the cohort and/or cohort qualifiers. In embodiments, the Comparative Statements 130 can be stored locally by the Cognitive Interpretation Application 105, or in one or more remote storage locations (such as in the cloud), as indicated by Comparison Storage 125. As illustrated, the Cognitive Interpretation Application 105 then performs Sentiment Analysis 135 on the extracted Comparative Statements 130, to generate a set of RESs 140. In an embodiment, this Sentiment Analysis 135 includes classifying each statement as positive, negative, or neutral with respect to each of the implicated therapies. In some embodiments, the Cognitive Interpretation Application 105 also determines a degree of the sentiment (based on, for example, the strength of the language or term used). Further, in some embodiments, the RESs 140 include an indication as to which outcome or outcome type the comparison relates to (e.g., overall survival, progression-free survival, etc.).

In some embodiments, the RESs 140 include an indication as to the therapies involved, the relevant cohort, and the like. In one embodiment, each RES 140 corresponds to a particular Comparative Statement 130. In one embodiment, each RES 140 is weighted based on a variety of factors. For example, in an embodiment, the weighting factors include how recently the corresponding document was published, whether the document has been peer-reviewed, the identity of the publisher or provider for the document, the number of patients evaluated in the clinical study, and the like. In one embodiment, publishers are associated with predefined weights or strengths, based on their prestige or trustworthiness. In some embodiments, the Cognitive Interpretation Application 105 weights each RES 140 based on a confidence level as well. In one embodiment, this confidence level is based in part on a confidence value returned by the NLP models. Further, in an embodiment, the confidence is adjusted based on where in the document the corresponding Comparative Statement 130 was found. For example, a comparison found in the abstract or conclusion can be given a higher weight, while a comparison found elsewhere in the document can be given a lower weight.

In the illustrated embodiment, the Knowledge Graph Component 110 retrieves these RESs 140 from the data store (as indicated by RES retrieval 145), and performs Graph Generation 150 to generate a Knowledge Graph 155. In an embodiment, each node in the Knowledge Graph 155 is a therapy (or combination of therapies), and each edge is based on the determined relationships and relative efficacies (e.g., the RESs 140). In one embodiment, the Knowledge Graph Component 110 adds an edge or connection for each determined RESs 140 (e.g., for each comparative statement found). In some embodiments, the Knowledge Graph Component 110 aggregates the comparisons. For example, in an embodiment, for each outcome type and cohort combination, the Knowledge Graph Component 110 can aggregate the corresponding RESs 140, in order to determine an overall relative efficacy for the therapies, with respect to the cohort and outcome. In some embodiments, this aggregation is based in part on the weights of each comparison, as discussed above.

Although not depicted in the illustrated embodiment, in some embodiments, the Cognitive Interpretation Application 105 also identifies statements relating to the efficacy or outcomes of a therapy, even in the absence of a comparison between therapies. In such an embodiment, the Cognitive Interpretation Application 105 can also perform Sentiment Analysis 135 on the non-comparative statements to determine whether the therapy is being referred to in a positive, neutral, or negative manner. In some embodiments, the Cognitive Interpretation Application 105 also determines the efficacy and/or outcomes of the therapy, if available in the Corpus 115. For example, in such an embodiment, the Cognitive Interpretation Application 105 can utilize NLP to determine what percentages of patients benefitted (with respect to each potential outcome), the magnitude of the benefits, and the like. In an embodiment, the Knowledge Graph Component 110 then incorporates these non-comparative statements into the Knowledge Graph 155 (e.g., by adding or refining a node corresponding to the therapy being discussed).

Figure 2:
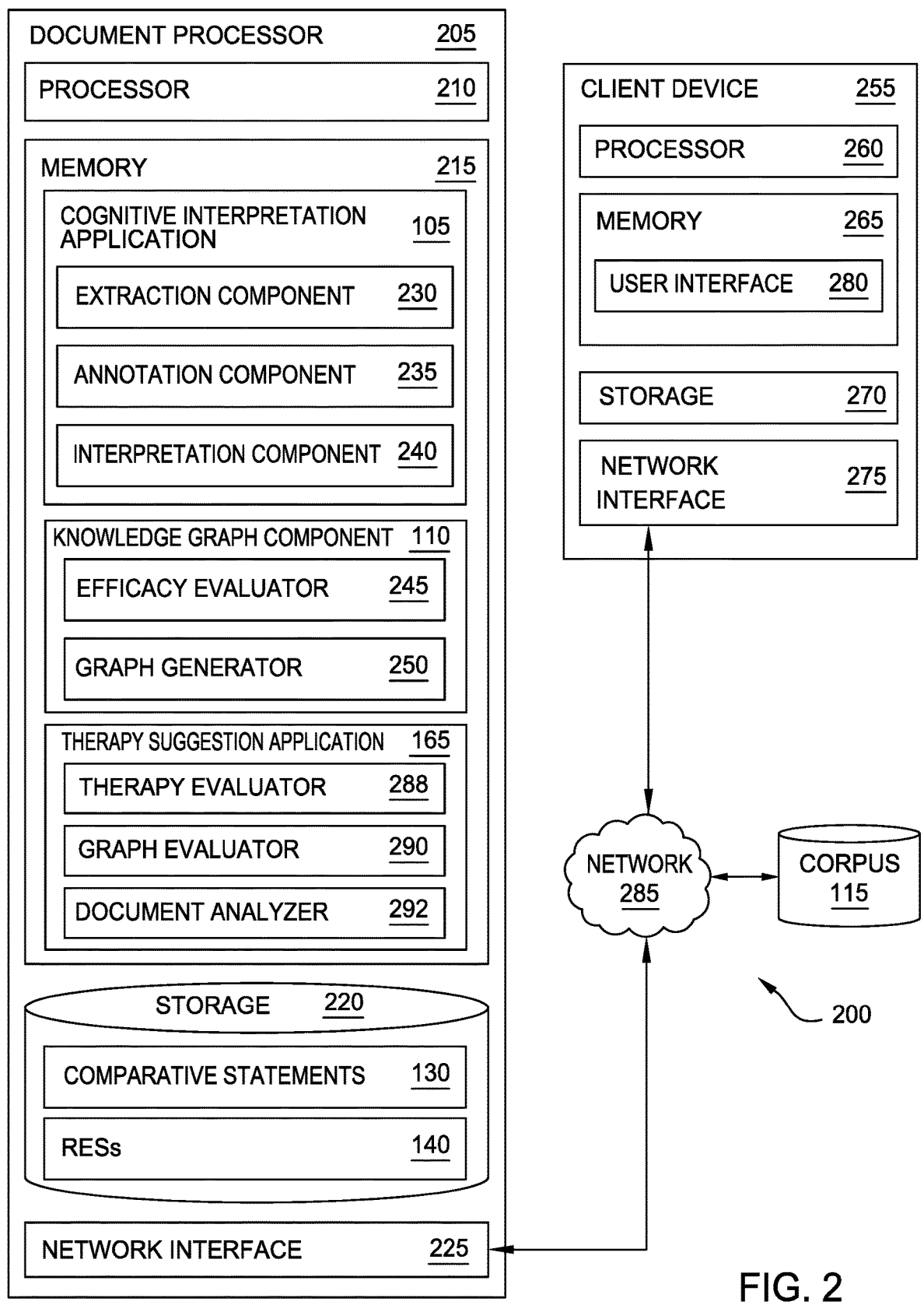
FIG. 2 is a block diagram of a system configured to cognitively determine the relative efficacy of therapies, according to one embodiment disclosed herein.

FIG. 2 is a block diagram of a system 200 configured to cognitively determine the relative efficacy of therapies, according to one embodiment disclosed herein. In the illustrated embodiment, the system 200 includes a Document Processor 205, a Client Device 255, and a Corpus 115. Although illustrated as discrete components, in embodiments, the Document Processor 205, Client Device 255, and Corpus 115 may operate or reside on a single device, or may be distributed across any number of devices. As illustrated, the Document Processor 205, Client Device 255, and Corpus 115 are communicatively linked through a Network 285. In one embodiment, the Network 285 is the Internet. Additionally, though a single Corpus 115 is illustrated, in embodiments, any number of corpora may be analyzed by the Document Processor 205.

As illustrated, the Document Processor 205 includes a Processor 210, a Memory 215, and Storage 220. In the illustrated embodiment, Processor 210 retrieves and executes programming instructions stored in Memory 215 as well as stores and retrieves application data residing in Storage 220. Processor 210 is representative of a single CPU, multiple CPUs, a single CPU having multiple processing cores, and the like. Memory 215 is generally included to be representative of a random access memory. Storage 220 may be a disk drive or flash-based storage device, and may include fixed and/or removable storage devices, such as fixed disk drives, removable memory cards, or optical storage, network attached storage (NAS), or storage area-network (SAN). Via the Network Interface 225, the Document Processor 205 can be communicatively coupled with corpuses of documents (such as Corpus 115), Client Devices 255, and the like.

In the illustrated embodiment, the Storage 220 of the Document Processor 205 includes a set of Comparative Statements 130 and RESs 140. In some embodiments, as discussed above, the Comparative Statements 130 and/or RESs 140 may be stored in one or more remote storage locations, such as in the cloud. Further, in some embodiments, the Storage 220 includes non-comparative statements as well. As discussed above, in an embodiment, the Comparative Statements 130 are annotated natural language text extracts from documents in the Corpus 115. In one embodiment, each Comparative Statement 130 includes a comparison or opinion of the author of the corresponding document. In some embodiments, the annotations indicate the qualifier or comparator used by the author, the therapies implicated by the statement, the cohort or cohort qualifiers that limit the applicability of the comparison, and the like. Further, in some embodiments, the Comparative Statements 130 include publication characteristics of the statements, such as the location in their corresponding documents where they were found, the date of the publication, the entity that published it, and the like. Additionally, in one embodiment, the Comparative Statements 130 include an indication as to the confidence value that the NLP model(s) generated when parsing the statements.

As discussed above, in one embodiment, each RES 140 is a data structure representing a particular Comparative Statement 130. In some embodiments, each RES 140 indicates the therapies involved, the directionality or sentiment of the comparison, the cohort implicated, and the like. Further, in an embodiment, each RES 140 includes a weight, which can be based on a variety of factors including the publication characteristics of the underlying Comparative Statement 130, the confidence of the NLP model(s), and the like. In some embodiments, the RESs 140 are configured to be searchable, such that other systems or components (such as the Knowledge Graph Component 110) can readily access the information, and obtain an up-to-date and comprehensive understanding of the current state of the literature.

In the illustrated embodiment, the Memory 215 of the Document Processor 205 includes a Cognitive Interpretation Application 105, a Knowledge Graph Component 110, and a Therapy Suggestion Application 165. The Cognitive Interpretation Application 105 includes an Extraction Component 230, an Annotation Component 235, and an Interpretation Component 240. Although depicted as discrete components for illustration, in embodiments, the operations and functionality of the Extraction Component 230, Annotation Component 235, and Interpretation Component 240 can be combined or divided across any number of components. Further, although depicted as software components residing in Memory 215, in embodiments, the operations and functionality of the Extraction Component 230, Annotation Component 235, and Interpretation Component 240 can be implemented using hardware, software, or a combination of hardware and software.

In an embodiment, the Extraction Component 230 identifies and extracts statements that include comparisons between therapies or treatment options from documents in the Corpus 115, as discussed above. In some embodiments, the Extraction Component 230 utilizes one or more NLP techniques or models to identify the relevant text. Further, in an embodiment, the Annotation Component 235 annotates the extracted statements. In one embodiment, the Annotation Component 235 utilizes predefined rules, and/or additional NLP models and/or techniques to annotate the statements. These annotated statements are then stored in the Comparative Statements 130. In this way, the textual comparisons found in the Corpus 115 are organized and represented in the Storage 220.

In the illustrated embodiment, the Interpretation Component 240 retrieves these Comparative Statements 130 and performs logical interpretation or sentiment analysis on them. In one embodiment, the Interpretation Component 240 classifies each Comparative Statement 130 as positive, negative, or neutral, with respect to each pair of involved therapies or treatments. For example, if the statement is that "treatment A led to better results than treatment B," the Interpretation Component 240 can determine that the comparison is positive with respect to treatment A, and negative with respect to treatment B. Similarly, if the statement is "treatments C and D were both inferior to treatment E," the Interpretation Component 240 determines that, as between therapies C and D, the sentiment is "neutral" or equal. However, as between treatment E and treatments C and D, the sentiment is positive. In this way, the Interpretation Component 240 determines the efficacy of each therapy, as compared to one or more other therapies in the statement.

In one embodiment, the Interpretation Component 240 also generates RESs 140 based on this analysis, as discussed below in more detail. That is, in an embodiment, the Interpretation Component 240 generates an organized and defined data structure that includes the relevant information from the textual Comparative Statement 130. In some embodiments, the Interpretation Component 240 generates a single RES 140 for each Comparative Statement 130. For example, in such an embodiment, if the sentiment is that treatment A is better than treatment B, the Interpretation Component 240 will generate a RES 140 indicating that treatment A is positive with respect to treatment B. In some embodiments, the Interpretation Component 240 also generates a second RES 140 indicating that treatment B is negative with respect to treatment A.

In the illustrated embodiment, the Knowledge Graph Component 110 generally retrieves the RESs 140 from Storage 220, and generates one or more knowledge graphs. As illustrated, the Knowledge Graph Component 110 includes an Efficacy Evaluator 245, and a Graph Generator 250. Although depicted as discrete components for illustration, in embodiments, the operations and functionality of the Efficacy Evaluator 245 and Graph Generator 250 can be combined or divided across any number of components. Further, although depicted as software components residing in Memory 215, in embodiments, the operations and functionality of the Efficacy Evaluator 245 and Graph Generator 250 can be implemented using hardware, software, or a combination of hardware and software. In an embodiment, the Efficacy Evaluator 245 retrieves and evaluates the RESs 140. For example, in one embodiment, the Efficacy Evaluator 245 searches for RESs 140 relating to one or more disorders or therapies that a user or administrator has selected. In other embodiments, the Efficacy Evaluator 245 retrieves and evaluates all available RESs 140. In an embodiment, the evaluation includes determining whether each RES 140 is already included in the knowledge graph.

Additionally, in some embodiments, the Efficacy Evaluator 245 aggregates the RESs 140 as appropriate, to determine an overall relative efficacy for each set of therapies. For example, in one embodiment, the Efficacy Evaluator 245 identifies RESs 140 with the same endpoints (e.g., that involve the same set of therapies) and aggregates them based on their respective weights to generate an overall relative efficacy between the therapies. In an embodiment, the Graph Generator 250 generates, inserts, and updates or refines nodes and edges in the knowledge graph, based on the evaluation provided by the Efficacy Evaluator 245. In some embodiments, the Graph Generator 250 and/or Efficacy Evaluator 245 aggregate the data by identifying all RESs 140 involving the same pair of therapies and including them in the graph, in order to capture all available evidence that compares the therapies without attempting to establish whether one is overall superior to the other.

In the illustrated embodiment, the Therapy Suggestion Application 165 includes a Therapy Evaluator 288, a Graph Evaluator 290, and a Document Analyzer 292. Although depicted as discrete components for illustration, in embodiments, the operations and functionality of the Therapy Evaluator 288, Graph Evaluator 290, and Document Analyzer 290 can be combined or divided across any number of components. Further, although depicted as software components residing in Memory 215, in embodiments, the operations and functionality of the Therapy Evaluator 288, Graph Evaluator 290, and Document Analyzer 290 can be implemented using hardware, software, or a combination of hardware and software.

In an embodiment, the Therapy Suggestion Application 165 analyzes the knowledge graph to identify and evaluate therapies that may be useful to treat patients. In the illustrated embodiment, the Therapy Evaluator 288 receives information relating to one or more patients, and identifies therapies that may be relevant. In one embodiment, the Therapy Evaluator 288 receives an indication of a particular patient or patient profile, and determines a corresponding cohort for the patient (e.g., based on attributes of the patient found in the patient profile, electronic medical records (EMRs), or specified by the healthcare provider or patient). In some embodiments, the Therapy Evaluator 288 receives an indication of one or more relevant cohorts for analysis.

Once the cohort is identified, in one embodiment, the Therapy Evaluator 288 determines a set of therapies that can be used to treat patients in the cohort that have the defined disorder or condition. In one embodiment, this includes retrieving a set of accepted therapies that has been previously defined for the cohort. In some embodiments, the Therapy Evaluator 288 analyzes the knowledge graph to identify potential therapies, and to find and evaluate evidence relating to the cohort (e.g., studies and trials that are relevant to the cohort). In one embodiment, the Therapy Evaluator 288 scores each potential therapy based on the connections and relationships found in the knowledge graph.

In some embodiments, prior to scoring a therapy, the Graph Evaluator 290 identifies the connections and edges (e.g., comparisons to other therapies) in the graph that are relevant to the therapy, identifies the relevant underlying documents, and refines or generates a revised weight or strength for the connection based on the underlying documents. Further, in the illustrated embodiment, the Document Analyzer 292 analyzes each of these underlying documents to generate a weight for the respective document, which is used by the Graph Evaluator 290 to refine the characteristics of the connection or edge. In this way, in one embodiment, the knowledge graph is revised or refined based on the attributes of the index patient. In the illustrated embodiment, the Therapy Evaluator 288 scores and ranks the therapies based on a variety of factors included in the refined or revised knowledge graph. For example, in one embodiment, the Therapy Evaluator 288 scores therapies based on how effective they are expected to be, and their (revised) relative efficacy as compared to each other.

In the illustrated embodiment, the Client Device 255 includes a Processor 260, a Memory 265, and Storage 270. In the illustrated embodiment, Processor 260 retrieves and executes programming instructions stored in Memory 265 as well as stores and retrieves application data residing in Storage 270. Processor 260 is representative of a single CPU, multiple CPUs, a single CPU having multiple processing cores, and the like. Memory 265 is generally included to be representative of a random access memory. Storage 270 may be a disk drive or flash-based storage device, and may include fixed and/or removable storage devices, such as fixed disk drives, removable memory cards, or optical storage, network attached storage (NAS), or storage area-network (SAN). Via the Network Interface 275, the Client Device 255 can be communicatively coupled with corpuses of documents (such as Corpus 115), Document Processor 205, and the like.

As illustrated, the Memory 265 of the Client Device 255 includes a User Interface 280 for interacting with the Corpus 115 and/or Document Processor 205. In an embodiment, the User Interface 280 includes a graphical user interface (GUI) that lets users or administrators retrieve and review documents in the Corpus 115. In some embodiments, the User Interface 280 also allows the user to select a subset of the Corpus 115 (e.g., via search queries) to be processed by the Document Processor 205.

Although not illustrated, in embodiments, the Cognitive Interpretation Application 105, Knowledge Graph Component 110, and Therapy Suggestion Application 165 each provide one or more application programming interfaces (APIs) that allow the user (through the User Interface 280) to control the operations of the components. For example, in an embodiment, the user can use the User Interface 280 and APIs to indicate the set of documents to be analyzed, and to adjust any settings or configurations of the Cognitive Interpretation Application 105. Further, in an embodiment, the User Interface 280 and APIs enable the user to review the Comparative Statements 130 and/or RESs 140. Additionally, in an embodiment, the User Interface 280 and APIs allow the user to direct the Knowledge Graph Component 110 to generate one or more knowledge graphs based on the RESs 140, and to analyze and parse the generated graphs. Additionally, in an embodiment, the APIs allow the user to access the Therapy Suggestion Application 165 to search for and receive evaluations for potential therapy options for patients.

Figure 3A:
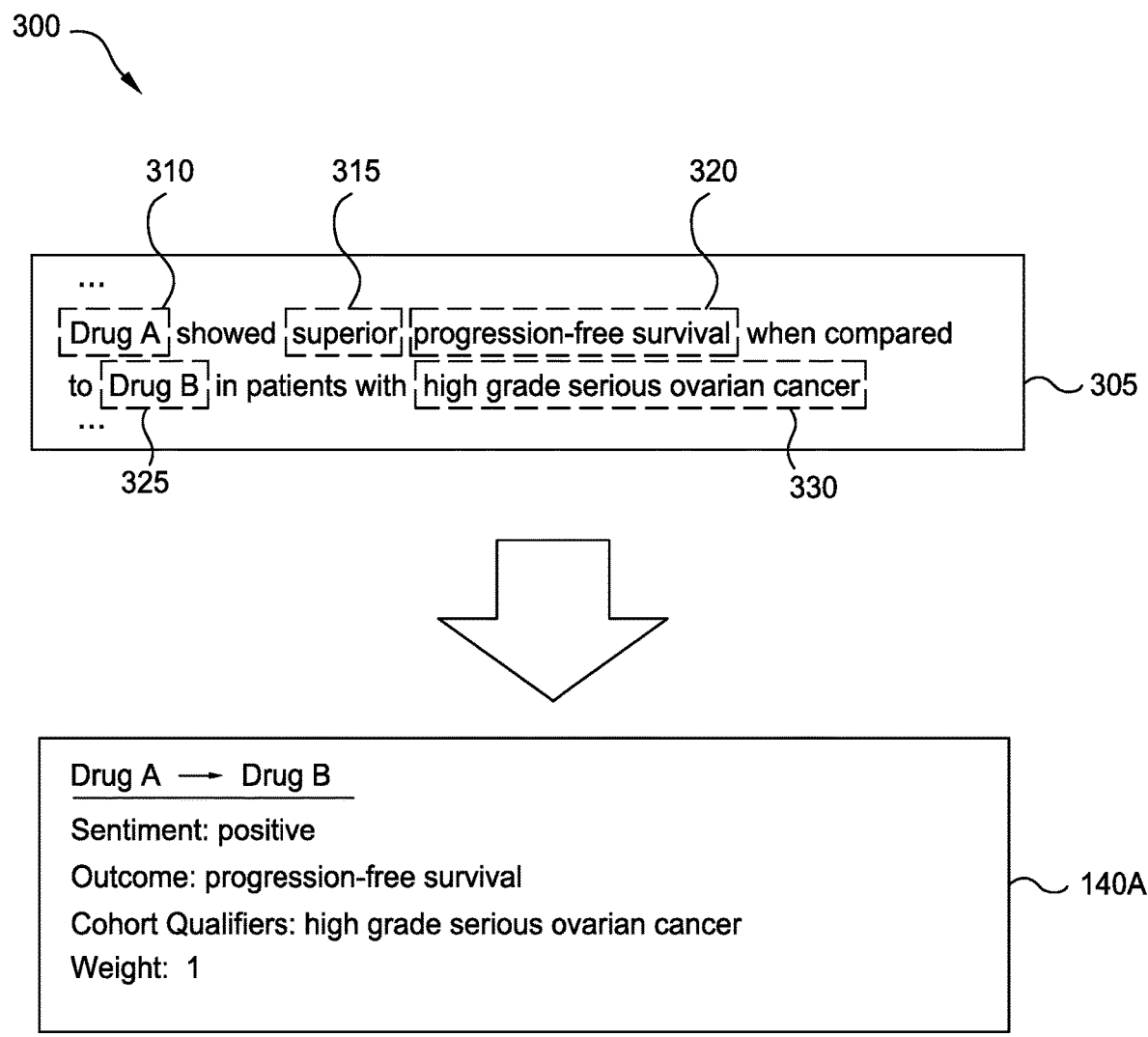
FIG. 3A is a workflow for determining the efficacy for a therapy, as compared to a different therapy, according to one embodiment disclosed herein.

FIG. 3A illustrates a workflow 300 for determining the efficacy for a therapy, as compared to a different therapy, according to one embodiment disclosed herein. In the illustrated workflow 300, a comparative statement (included in an Excerpt 305) is annotated with Annotations 310, 315, 320, 325, and 330. As illustrated by the ellipses above and below the comparative statement, the original document can be any size or length. In an embodiment, the Excerpt 305 was extracted from a document (e.g., by the Extraction Component 230) based on determining that it included a comparative statement.

In the illustrated embodiment, the Excerpt 305 was annotated by the Annotation Component 235, using one or more NLP techniques. As illustrated, Annotations 310 and 325 indicate the therapies mentioned or implicated by the statement. In one embodiment, these therapies are identified based on identifying the subject and object of the statement. Further, as illustrated, the Annotation 320 indicates the outcome (also referred to as the type) that is relevant to the statement. That is, in the illustrated embodiment, the Excerpt 305 discusses the relative efficacy of Drug A and Drug B, with respect to progression-free survival. Additionally, the Annotation 315 indicates the comparator (also referred to as qualifier or type qualifier), which indicates the comparison or statement being made (e.g., that the outcome, progression-free survival, was "superior."). Finally, as illustrated, the Annotation 330 corresponds to the cohort (or cohort qualifier) that the statement applies to.

In the illustrated embodiment, each of the relevant factors (e.g., Annotations 310, 315, 320, 325, and 330) are included within the same Excerpt 305. In embodiments, however, one or more of the relevant pieces of information can be located outside of the Excerpt 305. For example, in an embodiment, the cohort may be specified elsewhere in the document, and not explicitly given in the Excerpt 305. Similarly, one or more of the therapies or outcomes can be given elsewhere. For example, suppose the statement included "therapy Y led to the best results for the patients included in this study." In such an embodiment, the Extraction Component 230 and/or Annotation Component 235 can look elsewhere to determine the other therapy, the cohort, and the particular outcome type. Further, in an embodiment, the excerpt may only summarize one of the therapies in question and the Annotation Component 235 may look elsewhere to determine the complete definition of the therapy. For example, an excerpt may refer to "drug X-based therapy," where all of the components of this therapy are defined elsewhere in the document.

For example, the other therapies being tested may be listed in an introductory section, the cohort can be determined based on analyzing the patients involved, and the outcome of interest can be identified based on other sections of the document. In some embodiments, if the relevant information is not contained within the Excerpt 305, the confidence or weight of the comparative statement is reduced. In some embodiments, the Extraction Component 230 and/or Annotation Component 235 identify both the cohort (e.g., the patient population being studied) as well as cohort qualifiers (e.g., additional restrictions or limitations defining the group to whom the comparison is relevant). In one embodiments, the relevant cohort can identified based on other portions of the document (e.g., based on the abstract or study definitions). For example, a section of the document can indicate that the patients studied included females, aged 65-80, with hypertension. Additionally, the cohort qualifier ("high grade serious ovarian cancer") further restricts or limits the cohort to which the comparison is applicable.

As illustrated, the Cognitive Interpretation Component 105 (e.g., the Sentiment Component 240) then generates a RES 140A, based on the comparative statement. In the illustrated embodiment, as indicated by the arrow from Drug A to Drug B, the RES 140A indicates the relative efficacy of Drug A, as compared to Drug B. As illustrated, the sentiment is "positive," indicating that Drug A is better than Drug B with respect to the indicated cohort and the indicated outcome. Further, as illustrated, the outcome is "progression-free survival," and the cohort is individuals with "high grade serious ovarian cancer." As discussed above, in embodiments, this cohort can include additional attributes or definition, in combination with the cohort qualifiers found in the statement. Additionally, in the illustrated embodiment, the RES 140A includes a weight. In embodiments, this weight is based on a variety of factors, including the confidence of the NLP, the publication characteristics of the document, and the like.

Figure 3B:
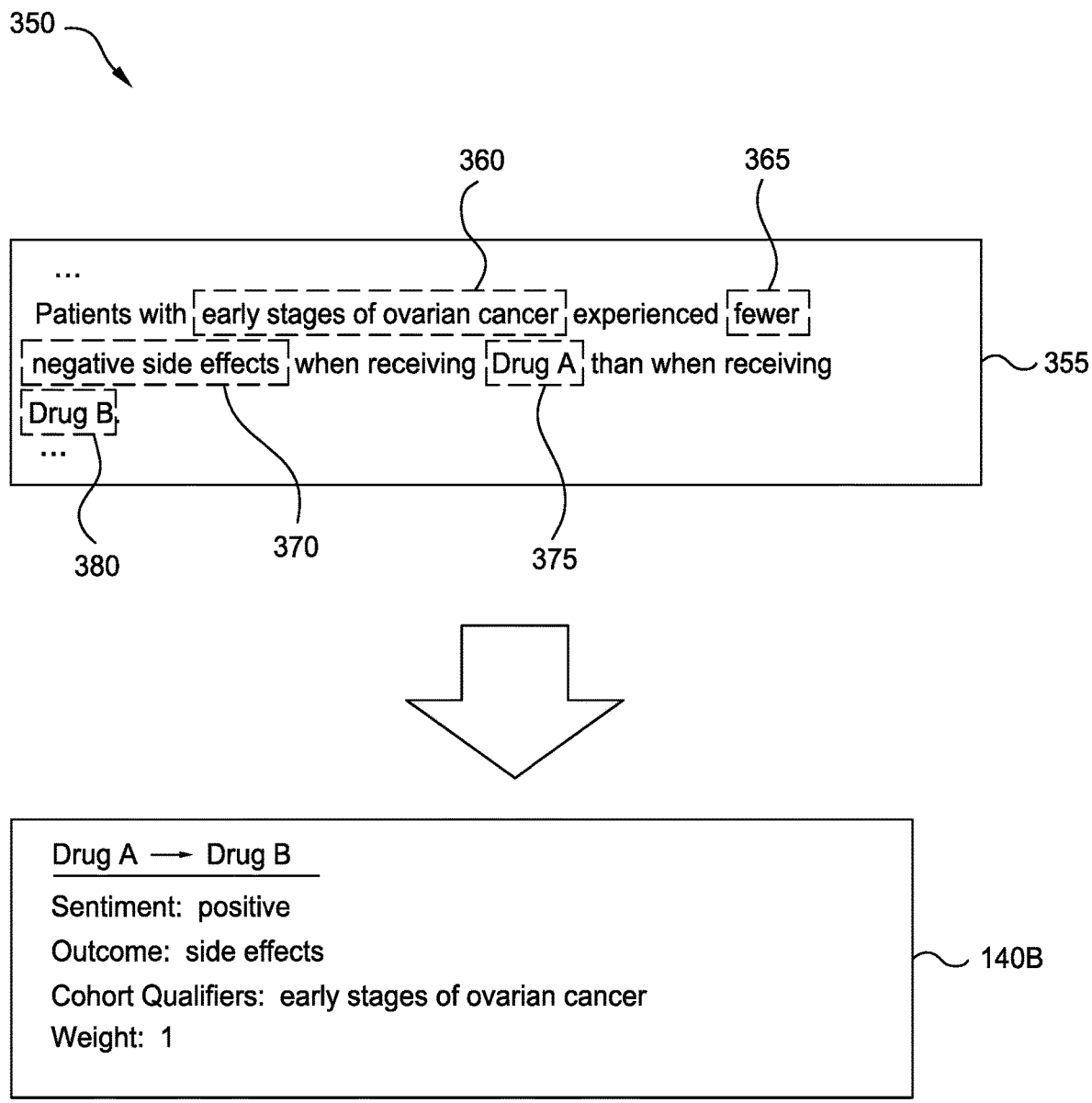
FIG. 3B illustrates a workflow for determining the efficacy for a therapy, as compared to a different therapy, according to one embodiment disclosed herein.

FIG. 3B illustrates a workflow 350 for determining the efficacy for a therapy, as compared to a different therapy, according to one embodiment disclosed herein. In the illustrated workflow 350, a comparative statement (included in an Excerpt 355) is annotated with Annotations 360, 365, 370, 375, and 380. As illustrated by the ellipses above and below the comparative statement, the original document can be any size or length. In an embodiment, the Excerpt 355 was extracted from a document (e.g., by the Extraction Component 230) based on determining that it included a comparative statement.

In an embodiment, the Excerpt 355 was annotated by the Annotation Component 235, using one or more NLP techniques. In the illustrated embodiment, Annotations 375 and 380 indicate the therapies mentioned or implicated by the statement. In one embodiment, these therapies are identified using the NLP models or techniques. Further, as illustrated, the Annotation 370 indicates the outcome of interest (also referred to as the type) that is relevant to the statement. That is, in the illustrated embodiment, the Excerpt 355 discusses the relative efficacy of Drug A and Drug B, with respect to negative side effects. Additionally, the Annotation 365 indicates the comparator (also referred to as qualifier or type qualifier), which indicates the comparison or statement being made (e.g., that the outcome, negative side effects, was "fewer."). Finally, as illustrated, the Annotation 360 corresponds to the cohort (or cohort qualifier) that the statement applies to.

As illustrated, the Cognitive Interpretation Component 105 (e.g., the Sentiment Component 240) then generates a RES 140B, based on the comparative statement. In the illustrated embodiment, as indicated by the arrow from Drug A to Drug B, the RES 140B indicates the relative efficacy of Drug A, as compared to Drug B. As illustrated, the sentiment is "positive," indicating that Drug A is better than Drug B with respect to the indicated cohort and the indicated outcome. That is, because the outcome itself is negative, the Sentiment Component 240 determines that a "worse" result in terms of the number or magnitude of side effects is, in fact, a positive result. Further, as illustrated, the outcome is "toxicity," and the cohort is individuals with "early stages of ovarian cancer." Additionally, in the illustrated embodiment, the RES 140B includes a weight. In embodiments, this weight is based on a variety of factors, including the confidence of the NLP, the publication characteristics of the document, and the like.

Figure 4:
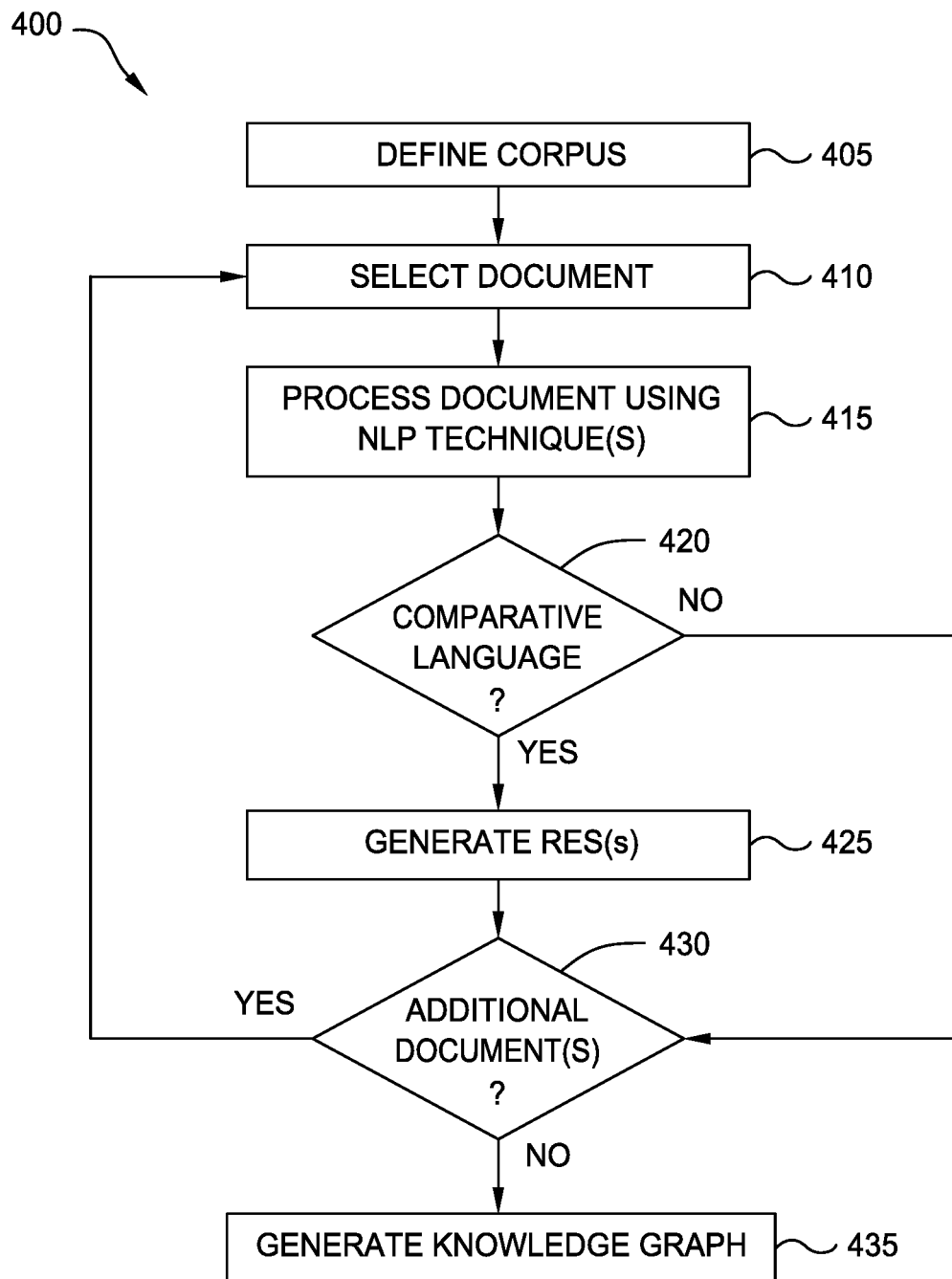
FIG. 4 illustrates a flow diagram illustrating a method for determining relative efficacies of various therapies, according to one embodiment disclosed herein.

FIG. 4 is a flow diagram illustrating a method 400 for determining relative efficacies of various therapies, according to one embodiment disclosed herein. The method 400 begins at block 405, where the Cognitive Interpretation Application 105 defines the relevant corpus. In one embodiment, this is based on a corpus indicated by the user or administrator. In some embodiments, the Cognitive Interpretation Application 105 receives one or more search terms, and builds the relevant corpus by searching or querying a larger corpus based on the search terms. In some embodiments, the Cognitive Interpretation Application 105 determines a set of documents in the identified corpus or sub-corpus that have not yet been processed or ingested. For example, in one embodiment, a user can indicate a disorder or search term, and the Cognitive Interpretation Application 105 can first identify documents relating to the indicated terms, and then identify documents in the corpus that have not already been processed and ingested. In this way, the Cognitive Interpretation Application 105 can selectively analyze new documents in order to update and refine the knowledge base. Once the relevant corpus has been defined, the method 400 proceeds to block 410.

At block 410, the Cognitive Interpretation Application 105 selects a document from the corpus. At block 415, the Cognitive Interpretation Application 105 processes the all or a portion of the selected document using one or more NLP techniques. As discussed above, in some embodiments, the Cognitive Interpretation Application 105 analyzes specified portions of each document. In some embodiments, if no comparisons are found (or if one or more identified comparative statements are missing information or detail), the Cognitive Interpretation Application 105 can process additional sections or text. In one embodiment, the Cognitive Interpretation Application 105 also annotates the extracted excerpts during block 415. The method 400 then proceeds to block 420.

At block 420, the Cognitive Interpretation Application 105 determines whether the selected document (or the portion that was analyzed) includes any comparative statements. If so, the method 400 continues to block 425. If not, the method 400 proceeds to block 430. At block 425, the Cognitive Interpretation Application 105 generates one or more RESs 140 for each of the identified comparative statements found. The method 400 then continues to block 430. At block 430, the Cognitive Interpretation Application 105 determines whether there is at least one additional document in the corpus that is yet to be processed. If so, the method 400 returns to block 410. Otherwise, the method 400 continues to block 435, where the Knowledge Graph Component 110 generates (or updates) a knowledge graph.

Figure 5:
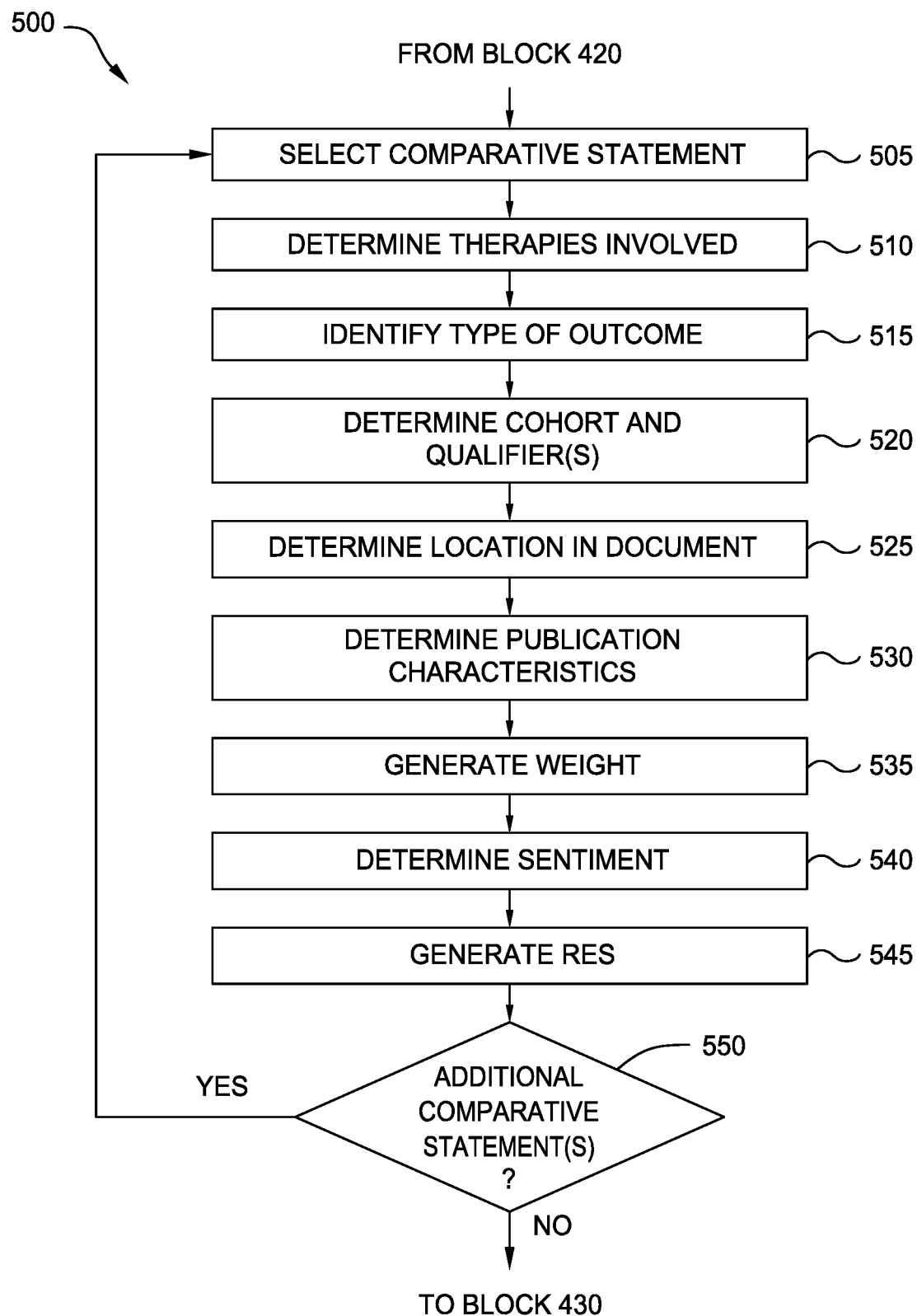
FIG. 5 is a flow diagram illustrating a method for generating relative efficacy structures summarizing comparisons between therapies, according to one embodiment disclosed herein.

FIG. 5 is a flow diagram illustrating a method 500 for generating RESs 140 summarizing comparisons between therapies, according to one embodiment disclosed herein. In one embodiment, the method 500 provides additional detail for block 425 in FIG. 4. The method 500 begins at block 505, where the Cognitive Interpretation Application 105 selects one of the comparative statements that were identified in the selected document. At block 510, the Cognitive Interpretation Application 105 identifies the therapies that are implicated by the selected statement. In one embodiment, the Cognitive Interpretation Application 105 utilizes NLP techniques to identify the relevant therapies. As discussed above, in some embodiments, the Cognitive Interpretation Application 105 parses other sections of the document, and/or other documents and data, in order to disambiguate any unknown or uncertain terms (e.g., ambiguous phrases or acronyms). The method 500 then continues to block 515.

At block 515, the Cognitive Interpretation Application 105 identifies the type of outcome the statement is addressing. That is, the Cognitive Interpretation Application 105 determines the particular outcome or effect that the selected statement is referring to. For example, in a medical embodiment, the outcomes can include overall survival, progression-free survival, remission, cure, death, complications, side effects, and the like. The method 500 then continues to block 520, where the Cognitive Interpretation Application 105 determines the cohort and/or cohort qualifiers that are relevant to the statement. For example, the cohort may be determined based on the patients being studied (e.g., as indicated by criteria used by the study authors when enrolling patients), and the cohort qualifiers can include any additional limitations included in the statement (e.g., "only patients above 65 saw a significant improvement.").

At block 525, the Cognitive Interpretation Application 105 determines the location in the selected document where the selected comparative statement was found. In one embodiment, block 525 comprises determining the section that the statement was in. In an embodiment, the sections are identified based on defined headings, metadata tags, and the like. In some embodiments, the weight of the generated RES 140 is adjusted based on the location. That is, in one embodiment, each section is associated with a respective weight or scale. For example, in one embodiment, the conclusion and abstract sections may be afforded higher weight than the general discussion section.

The method 500 then continues to block 530, where the Cognitive Interpretation Application 105 determines publication characteristics of the selected document that the statement was found in. For example, in one embodiment, the publication characteristics include a date when the document was published, the identity of the publisher, whether it has been peer-reviewed, and the like. In some embodiments, the publication characteristics also include the location in the document where the comparative statement was found. At block 535, the Cognitive Interpretation Application 105 generates a weight for the RES 140 based on the publication characteristics, and/or the determined location. In some embodiments, the Cognitive Interpretation Application 105 also considers any confidence values generated by the NLP models when parsing the text. Further, in one embodiment, the weight is based in part on the strength of the comparator used (e.g., whether the treatment is "slightly better" or "far superior").

The method 500 then continues to block 540, where the Cognitive Interpretation Application 105 determines the sentiment of the statement. In an embodiment, as discussed above, the Cognitive Interpretation Application 105 utilizes NLP to classify the statement as positive, negative, or neutral. Finally, at block 545, the Cognitive Interpretation Application 105 generates a RES 140 for the selected comparative statement based on the determined attributes, sentiment, and weight. At block 550, the Cognitive Interpretation Application 105 determines whether there is at least one additional comparative statement found in the document. If so, the method 500 returns to block 505. Otherwise, the method 500 terminates.

Figure 6:
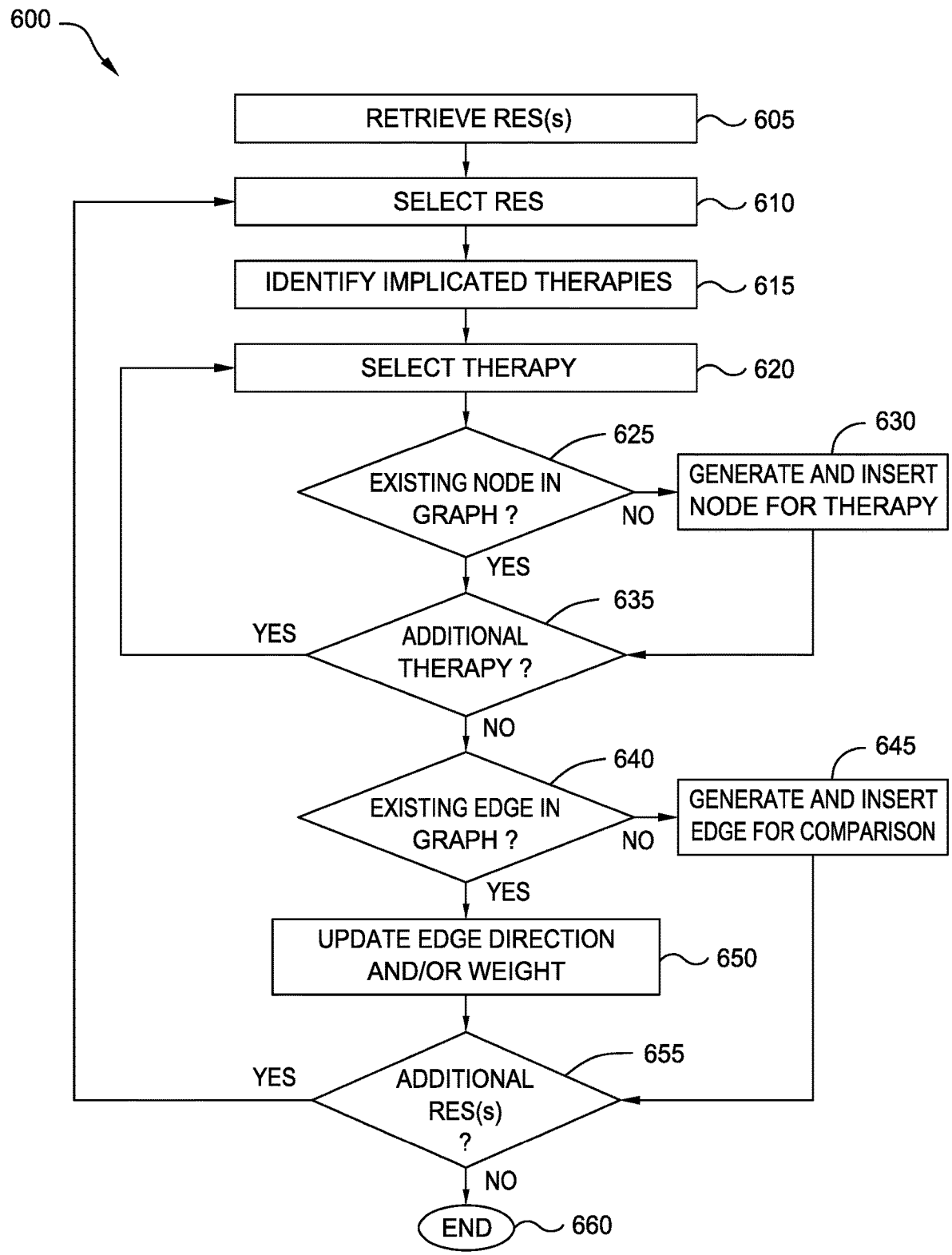
FIG. 6 is a flow diagram illustrating a method for generating a knowledge graph based on generated relative efficacy structures, according to one embodiment disclosed herein.

FIG. 6 is a flow diagram illustrating a method 600 for generating a knowledge graph based on generated relative efficacy structures, according to one embodiment disclosed herein. The method 600 begins at block 605, where the Knowledge Graph Component 110 retrieves one or more RES(s) 140 that were generated by the Cognitive Interpretation Application 105. At block 610, the Knowledge Graph Component 110 selects one of the RESs 140. The method 600 then proceeds to block 615, where the Knowledge Graph Component 110 identifies the therapies that are indicated by the selected RES 140. That is, the Knowledge Graph Component 110 determines which therapies are compared in the RES 140. At block 620, the Knowledge Graph Component 110 selects one of these identified therapies.

The method 600 continues to block 625, where the Knowledge Graph Component 110 determines whether there is an existing node in the knowledge graph for the selected therapy. As discussed above, in an embodiment, each node in the knowledge graph corresponds to a therapy. In some embodiments, a therapy can include a combination of treatments or mediations (e.g., a drug as well as physical therapy). If the selected therapy is already represented in the knowledge graph, the method 600 continues to block 635. If the selected therapy is not yet in the knowledge graph, the method 600 proceeds to block 630, where the Knowledge Graph Component 110 generates and inserts a new node into the graph to represent the selected therapy. The method 600 then continues to block 635.

At block 635, the Knowledge Graph Component 110 determines whether there are additional therapies in the selected RES 140. If so, the method 600 returns to block 620. Otherwise, the method 600 continues to block 640. In the illustrated embodiment, the Knowledge Graph Component 110 analyzes each therapy, and generates new nodes for each. In some embodiments, the knowledge graph is already constructed using a known or defined set of therapies. In such an embodiment, the Knowledge Graph Component 110 does not generate and insert new nodes. In some embodiments, in addition to an existing set of therapies, the Knowledge Graph Component 110 can further generate and insert nodes representing new therapies or new combinations of treatments that are identified in the RES 140.

In one embodiment, each node in the knowledge graph can be connected to zero or more other nodes, based on whether a comparison has been identified between the corresponding therapies. For example, in one embodiment, if two therapies have not been directly compared in the published literature, there will be no link or connection between the corresponding nodes. If, however, the therapies have been compared at least once, there will be an edge or connection between them. In some embodiments, each edge includes a number of dimensions indicating the directionality, the cohort(s) the edge applies to, the outcome(s) the edge applies to, and the like. For example, in such an embodiment, an edge may indicate that treatment A is better than treatment B, with respect to overall survival, in patients over 65. For patients under 65, however, there may be no edge or connection (if the therapies have not been compared for patients under 65), or there may be a link indicating that treatment B is better than treatment A. Similarly, with respect to a different outcome (such as progression-free survival or side effects), there may be no link, or a different link or connection may indicate that treatment B is better than treatment A. In some embodiments, the knowledge graph is constructed with a single edge connecting each pair of therapies, where that edge identifies all documents and/or RESs 140 that included a statement comparing the respective therapies. In another embodiment, the graph can include a respective edge to represent each respective RES 140 that is relevant to the respective pair of therapies.

In some embodiments, each edge in the graph is associated with a respective weight. This weight can be based on a variety of factors, including the number of times the relationship has been identified (e.g., the number of RESs 140 associated with the particular edge), the confidence or weight of each of those RESs 140, and the like. In some embodiments, as additional RESs 140 indicate the same relative efficacy (e.g., that one therapy is better than the other), the weight or strength of the edge is progressively strengthened. If, however, a RES 140 indicates the opposite comparison (e.g., that the first therapy is worse than the other), the weight or strength of the edge is reduced. In this way, each connection in the graph indicates an overall relative efficacy of the therapies, along with an associated strength or confidence in the accuracy of the comparison.

At block 640, the Knowledge Graph Component 110 determines whether there is an existing edge in the knowledge graph representing the relationship indicated by the selected RES 140. That is, in an embodiment, the Knowledge Graph Component 110 determines whether there is any link or connection between the identified therapies, with respect to the indicated cohort and outcome, regardless of the directionality of the relationship (e.g., regardless of whether the existing link matches the determined relative efficacy in the RES 140). In an embodiment, there may be any number of connections between the identified therapies with respect to other cohorts or other outcomes. The determination at block 640, however, is specific to the particular cohort and outcome specified in the RES 140.

In some embodiments, a particular RES 140 can include multiple comparisons. For example, if a statement included that treatment A was superior than all known treatments, the Cognitive Interpretation Application 105 can parse or analyze existing literature (or one or more knowledge graphs) to identify known treatments with respect to the disorder, cohort, and outcome. In such an embodiment, the RES 140 can include an indication of each of these known treatments. In other embodiments, a separate RES 140 is created for each of the comparisons (e.g., for each of the known treatments). In an embodiment, if the RES 140 includes comparisons to multiple therapies, the process discussed below (and reflected by blocks 640, 645, and 650) is repeated for each.

If the Knowledge Graph Component 110 determines, at block 640, that there is no edge in the graph representing the comparison, with respect to the identified cohort and outcome, the method 600 continues to block 645, where the Knowledge Graph Component 110 generates and inserts one. In one embodiment, the directionality of the new edge is based on the sentiment reflected in the selected RES 140 (e.g., positive, negative, or neutral). Further, in an embodiment, the initial weight or strength of the new edge is based on the weight or confidence of the RES 140. In this way, the knowledge graph is updated to reflect that the published literature includes a direct comparison between the therapies, and indicates the relative efficacy of the therapies (e.g., based on the directionality of the edge).

If the Knowledge Graph Component 110 determines, at block 640, that an edge already exists for the indicated comparison, with respect to the specified cohort and outcome, the method 600 continues to block 650, where the Knowledge Graph Component 110 updates the weight and/or direction of the identified edge. In some embodiments, the Knowledge Graph Component 110 instead inserts a new edge, depending on the particular design that will be used to represent multiple comparisons between two treatments in the knowledge graph. As discussed above, in one embodiment, this updating includes adjusting the weight of the edge based on the weight and directionality of the selected RES 140. In an embodiment, if the sentiment reflected by the RES 140 is in the same direction as the existing edge (e.g., the RES 140 and the edge agree that one treatment is superior), the weight or strength is increased. If the directions are opposite, the weight is decreased. Similarly, in one embodiment, if the selected RES 140 has a neutral sentiment (indicating that the therapies are equally effective), the weight of the edge is reduced, regardless of which direction it currently points. If the edge is already neutral, a neutral weight or strength can be increased, indicating that there is additional evidence that the therapies are equally effective.

In one embodiment, the amount that the edge strength is changed is dependent on the magnitude of the confidence or weight associated with the RES 140. If the RES 140 is associated with a high weight, the strength of the edge will be adjusted a greater amount than if the weight of the RES 140 was low. In one embodiment, if the weight falls below a predefined threshold (e.g., within a defined distance from zero), the edge is removed from the graph, indicating that there is no medical consensus regarding the relationship or relative efficacy. In other embodiments, the edge is updated to have no direction, reflecting that there is no solid consensus, and results are mixed (e.g., indicating that the comparison has been studied, but that there is no strong evidence supporting either therapy as more effective than the other). In some embodiments, this edge is retained with a low weight or strength, and is assigned a neutral sentiment to indicate that neither therapy is clearly superior to the other.

Similarly, in some embodiments, if an edge is neutral (or close to neutral) and the weight adjustment would cause the weight to be negative, the direction of the edge is switched, indicating a (potentially weak) new consensus that the relative efficacy of the treatments is reversed from the previously-understood comparison. In some embodiments, each edge in the graph is associated with a directionality as well as a weight or strength of the edge (representing the strength of the evidence). The method 600 then proceeds to block 655, where the Knowledge Graph Component 110 determines whether there is at least one additional RES 140 that has not been analyzed and ingested into the knowledge graph. If so, the method 600 returns to block 610 to select a next RES 140. Otherwise, the method 600 terminates at block 660. In this way, the Knowledge Graph Component 110 can update and refine the knowledge graph based on new therapies and studies. In embodiments, the knowledge graph is a multi-dimensional representation of the medical consensus as to relative efficacies of any number of therapies, with respect to any combination of particular cohorts and outcomes. Advantageously, embodiments of the present disclosure enable the graph to be continuously and rapidly updated when new published literature becomes available, such that the knowledge graph represents the most up-to-date and accurate representation possible. Further, because of the high-dimensionality of the graph (e.g., because the relative efficacies differ based on the individual cohort and outcome), the knowledge graph provides additional data that is far more granular, and is not otherwise available to healthcare providers.

In some embodiments, the knowledge graph can be accessed and searched by healthcare providers in order to determine optimal treatments for a particular patient. For example, in an embodiment, the provider can search the knowledge graph (e.g., using the User Interface 280 of the Client Device 255) to identify therapies and/or relative efficacies that are relevant to the cohort to which the patient belongs. That is, in an embodiment, the knowledge graph can be parsed to identify comparisons that are relevant to a patient in a particular cohort (e.g., having a particular set of attributes). In some embodiments, the provider can also filter, sort, or search the knowledge graph based on the desired outcome. In one embodiment, based on these relative efficacies, the therapies can be scored and ranked, in order to identify the most optimal therapy. This allows the provider to make improved decisions with respect to treating the patient.

In some embodiments, the outcomes types are associated with a predefined hierarchy. That is, some outcomes (e.g., progression-free survival) may be considered more important than other outcomes (e.g., side effects), and therefore be weighted more heavily when aggregating the relative efficacies with respect to each outcome in order to determine an overall relative efficacy (e.g., an overall optimal or best therapy, with respect to all outcomes). In such an embodiment, the ranking or scoring of the therapies may take into account the relative efficacies, as well as the importance or weight of the particular outcome. That is, although a first therapy may be the best with respect to side effects, it may be given a lower score than a second therapy that is better with respect to survival.

Although not illustrated, in some embodiments, the Knowledge Graph Component 110 can further generate nodes for which there are no existing comparisons. For example, if a paper or article includes a study of a particular therapy, but does not include any comparison to other therapies, the Knowledge Graph Component 110 can generate a node for the therapy, without necessarily connecting the node to any other therapies. Further, in some embodiments, the Knowledge Graph Component 110 includes an indication as to the efficacy of each therapy. For example, in such an embodiment, the Cognitive Interpretation Application 105 can determine the overall efficacy for each particular therapy, in addition to determining the relative efficacies of therapies, as compared to each other. This information can then be included in the corresponding node in the knowledge graph. In embodiments, the efficacy can include a percentage of patients who the therapy helped, and/or an amount that the therapy helped.

Figure 7:
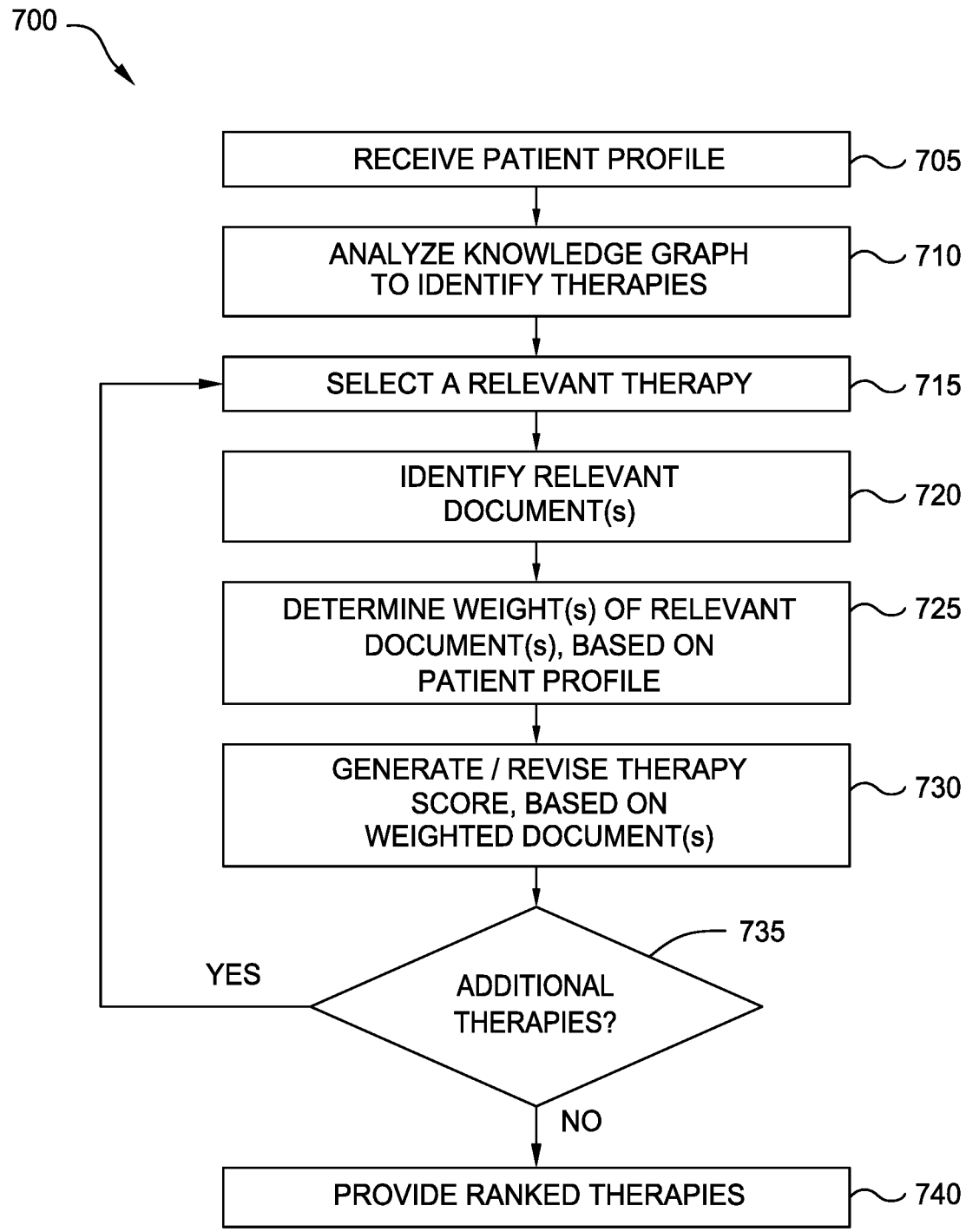
FIG. 7 is a flow diagram illustrating a method for analyzing therapy options utilizing a granular analysis of available documentation, according to one embodiment disclosed herein.

FIG. 7 is a flow diagram illustrating a method 700 for analyzing therapy options utilizing a granular analysis of available documentation, according to one embodiment disclosed herein. In the illustrated embodiment, the method 700 begins at block 705, where the Therapy Suggestion Application 165 receives a patient profile for an index patient. In an embodiment, the patient profile includes a set of attributes of the index patient. In some embodiments, the Therapy Suggestion Application 165 alternatively or additionally analyzes medical records or other sources of data to determine the relevant attributes of the patient. Further, in one embodiment, one or more attributes can be specified by the user or healthcare provider, or provided by the patient.

At block 710, the Therapy Suggestion Application 165 analyzes the knowledge graph to identify therapies that can be used to treat the relevant disorder, based on the attributes of the index patient. For example, in one embodiment, the Therapy Suggestion Application 165 analyzes the knowledge graph to identify therapies that have been tested or evaluated with respect to the disorder. In some embodiments, the Therapy Suggestion Application 165 identifies therapies that have been tested with individuals in the same or similar cohorts. The method 700 then continues to block 715, where the Therapy Suggestion Application 165 selects a first therapy to be evaluated. At block 720, the Therapy Suggestion Application 165 identifies the relevant documents that are associated with the selected therapy. For example, in an embodiment, the Therapy Suggestion Application 165 analyzes the knowledge graph to identify the underlying documents that were evaluated when generating the portion(s) of the graph that are related to the selected therapy. In one embodiment, this includes analyzing the documents used to generate or refine the connections or edges that are associated with the therapy (e.g., associated with the node that corresponds to the therapy), as well as the documents used to generate or refine the node itself (e.g., non-comparative statements).

The method 700 then proceeds to block 725, where the Therapy Suggestion Application 165 determines a weight for each of the identified documents, based on the patient profile (e.g., based on the attributes of the index patient). In an embodiment, the Therapy Suggestion Application 165 determines the aggregate value or distribution of values for each of the stated criteria in the respective document, and compares it to the value of the attribute with respect to the index patient. For example, in one embodiment, if "age" is one of the criteria, the Therapy Suggestion Application 165 can determine the average age of the trial participants, the range of ages of the participants, the distribution (e.g., mean and standard deviation) of the ages, and the like.

Further, in some embodiments, at block 725, the Therapy Suggestion Application 165 also determines the weight of each respective document based on any shared attributes of the participants. For example, if a threshold number or percentage of the participants have the same value (or a value within a defined range) for a particular attribute, the Therapy Suggestion Application 165 may determine whether the index patient's attributes align with this value or range, even if the attribute is not one of the stated criteria. In this way, the Therapy Suggestion Application 165 can determine a weight for each document based on a more granular understanding of how relevant it is to the index patient.

In some embodiments, the Therapy Suggestion Application 165 also considers documents where the index patient does not align perfectly with the stated cohort. In one embodiment, the Therapy Suggestion Application 165 can determine a number or percentage of the stated criteria that the patient satisfies, and weight the document based on how closely the patient aligns. For example, if the patient satisfies three out of five criteria for a first study and all six criteria for a second study, the Therapy Suggestion Application 165 can assign a relatively lower weight to the first study than to the second. In this way, the therapies are evaluated based on how relevant each individual study or document is to the index patient.

The method 700 then proceeds to block 730, where the Therapy Suggestion Application 165 generates or revises a score for the selected therapy, based on the relevant documents (and their respective revised weights). In one embodiment, this score reflects the potential efficacy of the therapy (with respect to the indicated patient), such that the Therapy Suggestion Application 165 can identify the most optimal treatments. At block 735, the Therapy Suggestion Application 165 then determines whether there is at least one remaining therapy to be evaluated at a granular level. If so, the method 700 returns to block 715. Otherwise, the method 700 proceeds to block 740, where the Therapy Suggestion Application 165 ranks or orders the therapies based on their respective scores, and provides them (e.g., to the user or healthcare provider). In some embodiments, the Therapy Suggestion Application 165 only provides therapies with a score exceeding a predefined threshold. In one embodiment, the Therapy Suggestion Application 165 provides a predefined number of therapies (e.g., the ten that scored highest).

Figure 8:
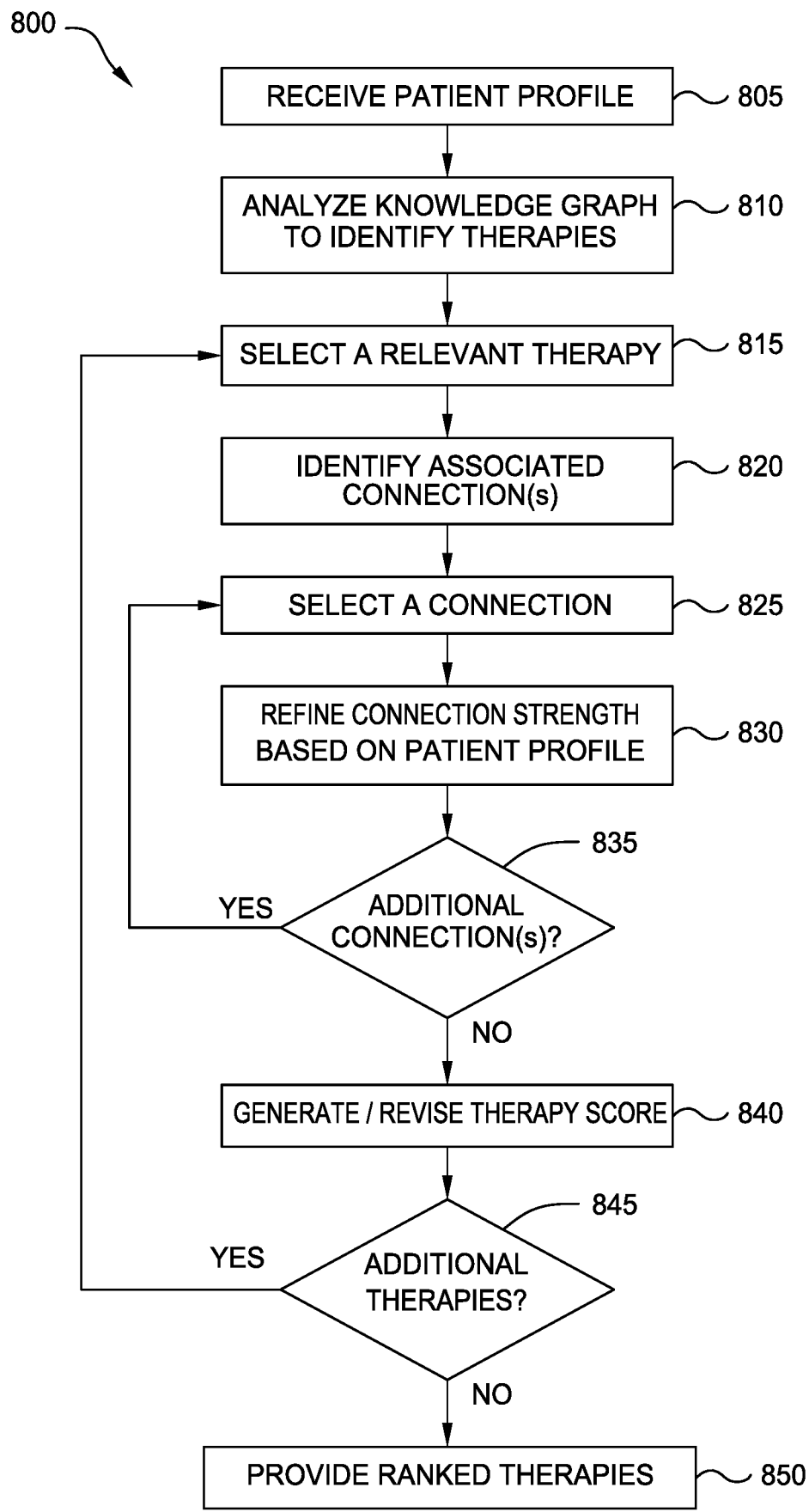
FIG. 8 is a flow diagram illustrating a method for analyzing therapy options utilizing a granular analysis of a knowledge graph, according to one embodiment disclosed herein.

FIG. 8 is a flow diagram illustrating a method 800 for analyzing therapy options utilizing a granular analysis of a knowledge graph, according to one embodiment disclosed herein. In an embodiment, the method 800 provides additional detail for the evaluation process discussed above with reference to FIG. 7. The method 800 begins at block 805, where the Therapy Suggestion Application 165 receives a patient profile for an index patient. As discussed above, in an embodiment, the patient profile includes a set of attributes of the index patient. Similarly, as discussed above, in some embodiments, the Therapy Suggestion Application 165 alternatively or additionally analyzes medical records or other sources of data to determine the relevant attributes of the patient. Further, in one embodiment, one or more attributes can be specified by the user or healthcare provider, or provided by the patient.

At block 810, the Therapy Suggestion Application 165 analyzes the knowledge graph to identify therapies that can be used to treat the relevant disorder. For example, in one embodiment, the Therapy Suggestion Application 165 analyzes the knowledge graph to identify therapies that have been tested or evaluated to treat the disorder. In some embodiments, the Therapy Suggestion Application 165 searches for therapies that have been tested with respect to individuals in the same or similar cohorts. The method 800 then continues to block 815, where the Therapy Suggestion Application 165 selects a first therapy to be evaluated. At block 820, the Therapy Suggestion Application 165 identifies the node that corresponds to the selected therapy, and identifies the edges or connections in the knowledge graph that are associated with the node. That is, the Therapy Suggestion Application 165 identifies the edges where the identified node is at one end point of the edge (e.g., indicating that the edge corresponds to a comparison between the selected therapy and one or more other therapies).

The method 800 then proceeds to block 825, where the Therapy Suggestion Application 165 selects a first of these identified connections. At block 830, the Therapy Suggestion Application 165 refines the strength of the selected connection based on the received patient profile (e.g., based on the patient attributes) and the attributes reflected in the underlying documents. This block is discussed in more detail below, with reference to FIGS. 9 and 10. The method 800 then proceeds to block 835, where the Therapy Suggestion Application 165 determines whether there is at least one additional relevant connection to be analyzed. If so, the method 800 returns to block 825 to select the next connection. Otherwise, the method 800 proceeds to block 840.

At block 840, the Therapy Suggestion Application 165 generates or revises the score of the selected therapy, based on the revised connections (e.g., based on the revised strengths of each relevant connection). In one embodiment, generating the score includes aggregating the relative efficacies (as represented by the edges or connections) based on the strengths of each. In an embodiment, the Therapy Suggestion Application 165 determines how effective the selected therapy is likely to be for the index patient, relative to other therapies in the knowledge graph, based on these revised connections (e.g., based on the strength and directionality of each connection). Further, in some embodiments, the score of the selected therapy is based in part on the relevant outcomes (e.g., based on which outcome(s) the user is most interested in). In some embodiments, the score is based on a weighted hierarchy of outcome types, in addition to the predicted efficacy with respect to each outcome type.

The method 800 then proceeds to block 845, where the Therapy Suggestion Application 165 determines whether there is at least one additional therapy that is yet to be evaluated. If so, the method 800 returns to block 815. Otherwise, the method 800 continues to block 850. At block 850, the Therapy Suggestion Application 165 ranks/sorts the therapies based on their respective scores, and provides the sorted therapies (e.g., to a user). In some embodiments, as discussed above, the Therapy Suggestion Application 165 only provides therapies with a score exceeding a predefined threshold. Further, in one embodiment, the Therapy Suggestion Application 165 provides a predefined number of therapies (e.g., the ten that scored highest).

Figure 9:
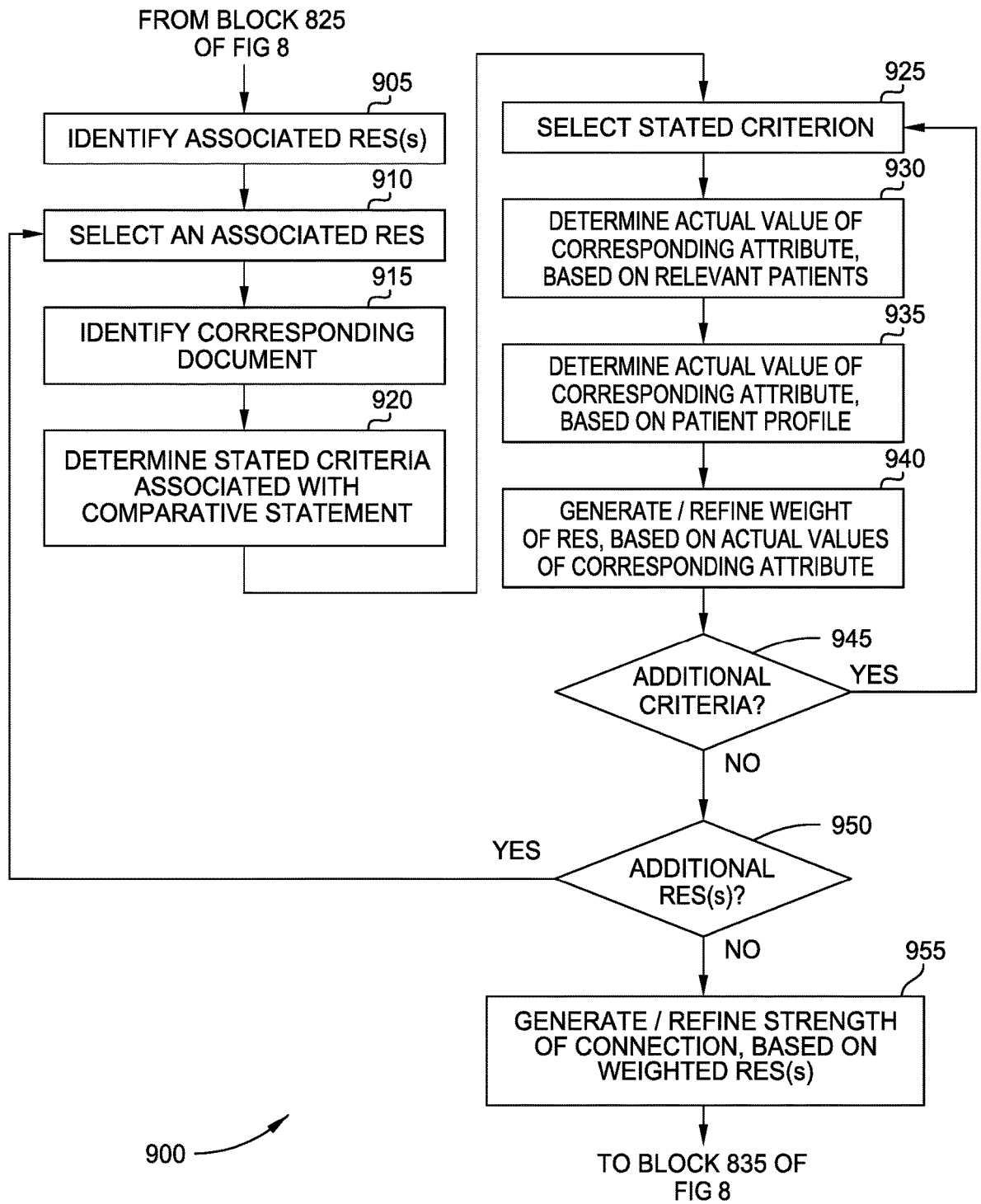
FIG. 9 is a flow diagram illustrating a method for analyzing and modifying a knowledge graph based on granular data, according to one embodiment disclosed herein.

FIG. 9 is a flow diagram illustrating a method 900 for analyzing and modifying a knowledge graph based on granular data, according to one embodiment disclosed herein. In an embodiment, the method 900 provides additional detail for block 830 of FIG. 8. The method 900 begins at block 905, where the Therapy Suggestion Application 165 identifies one or more RESs that are associated with the selected connection or edge in the knowledge graph. As discussed above, in an embodiment, each edge or connection is generated or refined based on one or more RESs, where each RES corresponds to a comparative statement made in the published literature. In some embodiments, each connection includes an indication as to the underlying RES(s) that were used to generate the edge. The method 900 then proceeds to block 910.

At block 910, the Therapy Suggestion Application 165 selects one of the identified RESs. At block 915, the Therapy Suggestion Application 165 identifies the document that corresponds to the selected RES. As discussed above, in an embodiment, each RES was generated based on a comparative statement found in a document in a corpus of published literature. In some embodiments, each RES includes an indication and/or link to the corresponding document, and/or to the location in the document that the comparative statement was identified. The method 900 then proceeds to block 920, where the Therapy Suggestion Application 165 determines the stated criteria in the document that is associated with the comparative statement. In one embodiment, the Therapy Suggestion Application 165 does so by analyzing the comparative statement itself to identify the relevant cohort and cohort qualifiers, as discussed above. In some embodiments, the Therapy Suggestion Application 165 identifies the stated criteria of the overall document (e.g., the criteria that was used to enroll or reject participants). In some embodiments, the Therapy Suggestion Application 165 determines the criteria based on the information included in the selected RES.

The method 900 then proceeds to block 925, where the Therapy Suggestion Application 165 selects one of the identified criteria. At block 930, the Therapy Suggestion Application 165 determines an actual value of the attribute that corresponds to the selected criterion, based on the relevant patients in the study. That is, in the illustrated embodiment, the Therapy Suggestion Application 165 identifies and analyzes attributes for the participants in the study to which the comparative statement is relevant (e.g., all of the participants in the study, or the participants that are also included within any cohort qualifiers included in the comparative statement). For example, suppose the selected criterion (or the comparative statement) states that participants must be younger than 65 (or that the statement only applies to the participants who were under 65). In an embodiment, the Therapy Suggestion Application 165 determines that the corresponding attribute for this criterion is age, and therefore determines the age of each of the identified relevant participants.

In some embodiments, determining the actual value of the corresponding attribute includes aggregating the individual values from the identified patients. In one embodiment, aggregating the values includes determining the average or representative value. In some embodiments, aggregating the data includes determining the range or distribution of values. For example, in one embodiment, if the values are numeric, the Therapy Suggestion Application 165 computes the mean and standard deviation of the data. In some embodiments, the Therapy Suggestion Application 165 further determines the maximum and minimum values. Additionally, in one embodiment, if the data is categorical the Therapy Suggestion Application 165 determines the number of values presented by the identified patients, the number or percentage of participants who presented each category, the largest and/or smallest categories, and the like. For example, in an embodiment, if the criterion is "less than ten drinks per week of alcohol," the Therapy Suggestion Application 165 can determine the number or percentage of relevant participants that consume zero alcohol, the number or percentage that consume less than five drinks a week, and so on.

The method 900 then proceeds to block 935, where the Therapy Suggestion Application 165 determines the value of the corresponding attribute, with respect to the index patient. At block 940, the Therapy Suggestion Application 165 generates or refines the weight of the document (e.g., of the selected RES), based on the variance between the value of the attribute with respect to the index patient, and the value(s) of the attribute with respect to the study participants. That is, in an embodiment, the Therapy Suggestion Application 165 determines whether the patient's value aligns with the participant's aggregate value. For example, if the patient's attribute value matches the value of a minority of the relevant participants, the Therapy Suggestion Application 165 can determine that the weight should be reduced.

In some embodiments, the Therapy Suggestion Application 165 determines the weight based on whether the patient's value aligns with the aggregate participant value (e.g., whether it exactly matches, or is within a predefined range or distance). In some embodiments, the weight is further based on how much the values differ. For example, if the average age of the participants is 60 and the patient is 25, the weight will be relatively lower than if the patient was 50. Similarly, suppose the attribute is "number of cigarettes a week." Suppose further that 80% of the participants reported "zero," 10% reported "one to five," 5% reported "five to ten," and 5% reported "more than ten." If the patient's value is "five to ten," the RES will be assigned a lower weight than if the patient's value was "one to five," because the patient's value is further from the representative (e.g., majority) value of "zero".

In this way, the Therapy Suggestion Application 165 can determine a revised weight for the RES, based on a more granular analysis of the underlying data. Thus, in the illustrated embodiment, if the individuals that the comparative statement refers to are unlike the index patient, the weight or confidence in the usefulness of the comparative statement is reduced. In contrast, if the patient closely aligns with the actual participants, the confidence or weight of the RES can be increased. Notably, at block 940, the weight of the RES is adjusted based on the actual value of the relevant attribute, and is not based simply on whether the patient satisfies the stated criterion. The method 900 then proceeds to block 945, where the Therapy Suggestion Application 165 determines whether there is at least one additional criterion specified or stated with respect to the selected RES. If so, the method 900 returns to block 925. Otherwise, the method 900 continues to block 950.

At block 950, the Therapy Suggestion Application 165 determines whether there is at least one additional RES that is yet to be analyzed, with respect to the selected connection or edge. If so, the method 900 returns to block 910 to select the next RES. Otherwise, the method 900 continues to block 955. At block 955, the Therapy Suggestion Application 165 generates or refines the strength of the selected connection, based on the revised weighted RESs. For example, as discussed above, in some embodiments, each edge in the knowledge graph is generated and refined based on the weight and value of each RES. Thus, in the illustrated embodiment, the Therapy Suggestion Application 165 re-generates the connection (e.g., determines a revised strength and/or directionality for the connection) based on the revised weights of the component RESs. The method 900 then terminates.

Figure 10:
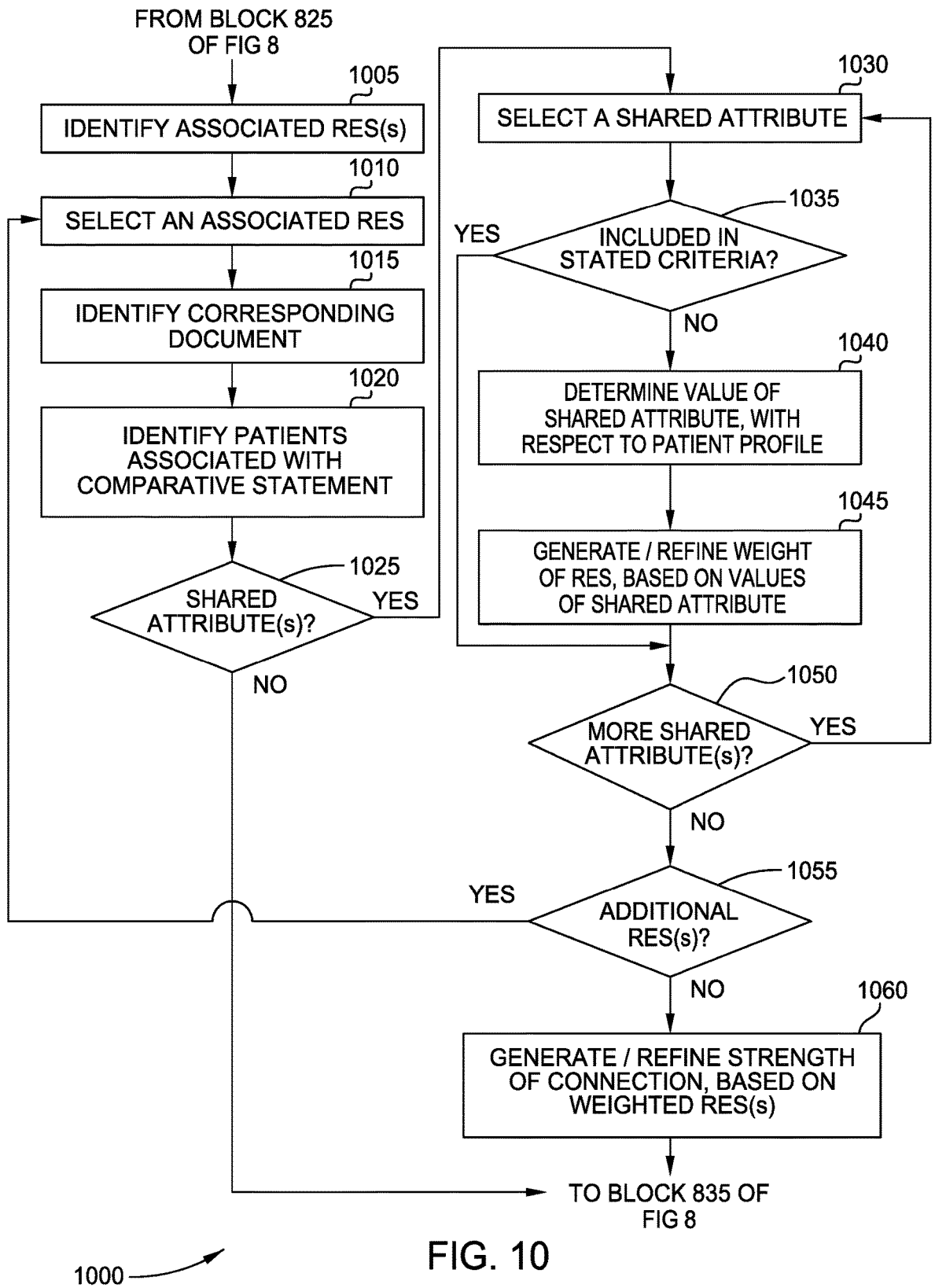
FIG. 10 is a flow diagram illustrating a method for analyzing and modifying a knowledge graph based on granular data, according to one embodiment disclosed herein.

FIG. 10 is a flow diagram illustrating a method 1000 for analyzing and modifying a knowledge graph based on granular data, according to one embodiment disclosed herein. In an embodiment, the method 1000 provides additional detail for block 830 of FIG. 8. The method 1000 begins at block 1005, where the Therapy Suggestion Application 165 identifies one or more RESs that are associated with the selected connection or edge in the knowledge graph. As discussed above, in an embodiment, each edge or connection is generated or refined based on one or more RESs, where each RES corresponds to a comparative statement made in the published literature. In some embodiments, each connection includes an indication as to the underlying RES(s) that were used to generate the edge. The method 1000 then proceeds to block 1010.

At block 1010, the Therapy Suggestion Application 165 selects one of the identified RESs. At block 1015, the Therapy Suggestion Application 165 identifies the document that corresponds to the selected RES. As discussed above, in an embodiment, each RES was generated based on a comparative statement found in a document in a corpus of published literature. In some embodiments, each RES includes an indication and/or link to the corresponding document, and/or to the location in the document that the comparative statement was identified. The method 1000 then proceeds to block 1020, where the Therapy Suggestion Application 165 identifies the set of participants that are associated with the comparative statement. That is, in the illustrated embodiment, the Therapy Suggestion Application 165 identifies the participants in the study to which the comparative statement is relevant (e.g., all of the participants in the study, or the participants that are also included within any cohort qualifiers included in the comparative statement).

The method 1000 then proceeds to block 1025, where the Therapy Suggestion Application 165 determines whether there is at least one shared attribute among the identified relevant participants. That is, the Therapy Suggestion Application 165 determines one or more attributes of each relevant participant, and determines whether there are any attributes that are shared. In one embodiment, the attribute is shared if all of the relevant patients exhibit the same value. For example, if none of the relevant participants have hypertension, the Therapy Suggestion Application 165 can determine that the absence of hypertension is a shared attribute. In some embodiments, an attribute is shared if a threshold number or percentage of the relevant participants have the same value. Similarly, in one embodiment an attribute is a shared attribute if the standard deviation of the aggregate value is below a predefined threshold. In one embodiment, the Therapy Suggestion Application 165 limits this analysis to a predefined list of potential shared attributes. In other embodiments, the Therapy Suggestion Application 165 considers all attributes for which there is available data in the document.

If the Therapy Suggestion Application 165 determines that there are no shared attributes, the method 1000 terminates. If there is at least one shared attribute, the method 1000 proceeds to block 1030, where the Therapy Suggestion Application 165 selects one of the identified shared attributes. The method 1000 then continues to block 1035, where the Therapy Suggestion Application 165 determines whether the shared attribute is included in the stated criteria that are associated with the comparative statement. For example, if a criterion states that only individuals who do not consume alcohol are eligible for the study, it is not surprising that none of the relevant participants consume alcohol. Further, because it is included in the stated criteria, in some embodiments, the shared attribute is already considered when generating the weight for the RES. If the selected shared attribute is already reflected in the stated criteria, the method 1000 proceeds to block 1050. If not, the method 1000 continues to block 1040.

At block 1040, the Therapy Suggestion Application 165 determines the value of the shared attribute, with respect to the patient profile of the index patient. That is, the Therapy Suggestion Application 165 determines the index patient's value for the shared attribute. The method 1000 then proceeds to block 1045, where the Therapy Suggestion Application 165 generates or refines the weight of the selected RES, based on the variance between the patient's attribute value and the value of the shared attribute with respect to the relevant participants in the study. That is, in an embodiment, the Therapy Suggestion Application 165 determines whether the patient's value aligns with the shared value for the attribute.

In some embodiments, the Therapy Suggestion Application 165 determines the weight based on whether the patient's value aligns with the shared participant value (e.g., whether it exactly matches, or is within a predefined range or distance). In some embodiments, the weight is further based on how much the values differ. For example, suppose the shared attribute is age, the value with respect to the relevant participants is 55, with a standard deviation of five years. Suppose further that the patient is 25. In an embodiment, the weight of the RES will be relatively lower than if the patient was 50. Similarly, suppose the shared attribute is "number of cigarettes a week," and that 80% of the participants reported "zero." If the patient's value is "five to ten," the RES will be assigned a lower weight than if the patient's value was "one to five," because the patient's value is further from the representative or majority shared value (e.g., "zero").

The method 1000 then proceeds to block 1050, where the Therapy Suggestion Application 165 determines whether there is at least one additional shared attribute identified in the relevant participants. If so, the method 1000 returns to block 1030. Otherwise, the method 1000 continues to block 1055, where the Therapy Suggestion Application 165 determines whether there is at least one additional RES to be evaluated, with respect to the selected connection. If so, the method 1000 returns to block 1010. Otherwise, the method 1000 proceeds to block 1060. At block 1060, the Therapy Suggestion Application 165 generates or refines the strength value for the selected connection, based on the re-weighted RESs, as discussed above. The method 1000 then terminates.

Figure 11:
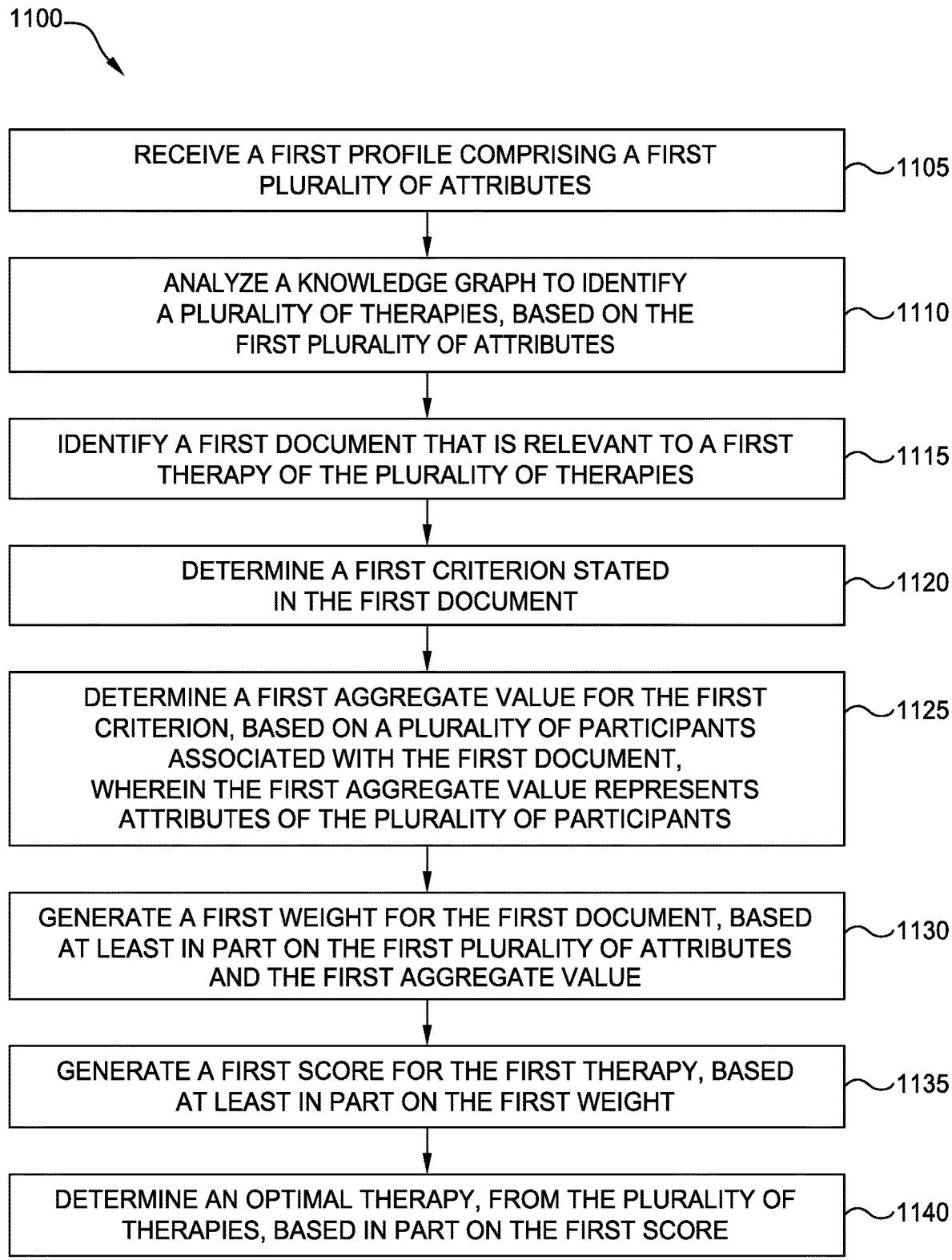
FIG. 11 is a flow diagram illustrating a method for providing therapy options utilizing granular analysis of the underlying data, according to one embodiment disclosed herein.

FIG. 11 is a flow diagram illustrating a method 1100 for providing therapy options utilizing granular analysis of the underlying data, according to one embodiment disclosed herein. The method 1100 begins at block 1105, where the Therapy Suggestion Application 165 receives a first profile comprising a first plurality of attributes. At block 1110, the Therapy Suggestion Application 165 analyzes a knowledge graph to identify a plurality of therapies, based on the first plurality of attributes. The method 1100 then proceeds to block 1115, where the Therapy Suggestion Application 165 identifies a first document that is relevant to a first therapy of the plurality of therapies. Further, at block 1120, the Therapy Suggestion Application 165 determines a first criterion stated in the first document. Further, at block 1125, where the Therapy Suggestion Application 165 determines a first aggregate value for the first criterion, based on a plurality of participants associated with the first document, wherein the first aggregate value represents attributes of the plurality of participants. The method 1100 then continues to block 1130, where the Therapy Suggestion Application 165 generates a first weight for the first document, based at least in part on the first plurality of attributes and the first aggregate value. Next, at block 1135, the Therapy Suggestion Application 165 generates a first score for the first therapy, based at least in part on the first weight. Finally, the method 1100 continues to block 1140, where the Therapy Suggestion Application 165 determines an optimal therapy, from the plurality of therapies, based in part on the first score.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the preceding, reference is made to embodiments presented in this disclosure. However, the scope of the present disclosure is not limited to specific described embodiments. Instead, any combination of the preceding features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the preceding aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access applications (e.g., the Therapy Suggestion Application 165) or related data available in the cloud. For example, the Therapy Suggestion Application 165 could execute on a computing system in the cloud and parse a knowledge graph to evaluate potential therapies. In such a case, the Therapy Suggestion Application 165 could evaluate studies on a granular basis, and store strengths, weights, and scores for documents, connections, and therapies at a storage location in the cloud. Doing so allows a user to access this information from any computing system attached to a network connected to the cloud (e.g., the Internet).

While the foregoing is directed to embodiments of the present invention, other and further embodiments of the invention may be devised without departing from the basic scope thereof, and the scope thereof is determined by the claims that follow.

What is claimed is:

1. A method comprising:
   receiving a first profile comprising a first plurality of attributes;
   analyzing a knowledge graph to identify a plurality of therapies, based on the first plurality of attributes;
   identifying a first document that is relevant to a first therapy of the plurality of therapies, comprising:
      identifying a first connection in the knowledge graph, wherein the first connection represents a comparison between the first therapy and at least one other therapy in the plurality of therapies; and
      determining that the first connection was generated based at least in part on the first document;
   determining a first criterion stated in the first document;
   determining a first aggregate value for the first criterion, based on a plurality of participants associated with the first document, wherein the first aggregate value represents attributes of the plurality of participants;
   generating a first weight for the first document, based at least in part on the first plurality of attributes and the first aggregate value;
   generating a first score for the first therapy, based at least in part on the first weight; and
   determining an optimal therapy, from the plurality of therapies, based in part on the first score.

2. The method of claim 1, wherein identifying the first document comprises:
   determining a first plurality of criteria stated in the first document; and
   determining whether the plurality of attributes of the first profile align with the first plurality of criteria.

3. The method of claim 1, wherein determining the first aggregate value for the first criterion comprises:
   identifying a first attribute that corresponds to the first criterion; and
   determining a distribution of values of the first attribute, with respect to the plurality of participants associated with the first document.

4. The method of claim 3, wherein determining the distribution of values of the first attribute, with respect to the plurality of participants associated with the first document comprises determining an average value of the first attribute.

5. The method of claim 3, wherein determining the first weight for the first document comprises:
   determining a first value of the first attribute based on the first profile;
   determining a variance between the first value and the first aggregate value; and
   refining the first weight based on the variance.

6. The method of claim 1, wherein generating the first score for the first therapy comprises determining a revised strength for the first connection, based on a plurality of studies associated with the first connection.

7. The method of claim 1, wherein generating the first weight for the first document further comprises:
   identifying a shared attribute that has a common value among the plurality of participants associated with the first document;
   determining that the shared attribute is not included in a first plurality of criteria specified in the first document;
   determining a first value of the shared attribute based on the first profile; and
   refining the first weight based on determining whether the first value matches the common value.

8. A computer-readable storage medium having computer-readable program code embodied therewith, the computer-readable program code executable by one or more computer processors to perform an operation comprising:

receiving a first profile comprising a first plurality of attributes;

analyzing a knowledge graph to identify a plurality of therapies, based on the first plurality of attributes;

identifying a first document that is relevant to a first therapy of the plurality of therapies, comprising:

identifying a first connection in the knowledge graph, wherein the first connection represents a comparison between the first therapy and at least one other therapy in the plurality of therapies; and determining that the first connection was generated based at least in part on the first document;

determining a first criterion stated in the first document;

determining a first aggregate value for the first criterion, based on a plurality of participants associated with the first document, wherein the first aggregate value represents attributes of the plurality of participants;

generating a first weight for the first document, based at least in part on the first plurality of attributes and the first aggregate value;

generating a first score for the first therapy, based at least in part on the first weight; and determining an optimal therapy, from the plurality of therapies, based in part on the first score.

9. The computer-readable storage medium of claim 8, wherein determining the first aggregate value for the first criterion comprises:

identifying a first attribute that corresponds to the first criterion; and determining a distribution of values of the first attribute, with respect to the plurality of participants associated with the first document.

10. The computer-readable storage medium of claim 9, wherein determining the first weight for the first document comprises:

determining a first value of the first attribute based on the first profile;

determining a variance between the first value and the first aggregate value; and refining the first weight based on the variance.

11. The computer-readable storage medium of claim 8, wherein generating the first score for the first therapy comprises determining a revised strength for the first connection, based on a plurality of studies associated with the first connection.

12. The computer-readable storage medium of claim 8, wherein generating the first weight for the first document further comprises:

identifying a shared attribute that has a common value among the plurality of participants associated with the first document;

determining that the shared attribute is not included in a first plurality of criteria specified in the first document;

determining a first value of the shared attribute based on the first profile; and refining the first weight based on determining whether the first value matches the common value.

13. A system comprising:

one or more computer processors; and a memory containing a program which when executed by the one or more computer processors performs an operation, the operation comprising:

receiving a first profile comprising a first plurality of attributes;

analyzing a knowledge graph to identify a plurality of therapies, based on the first plurality of attributes;

identifying a first document that is relevant to a first therapy of the plurality of therapies, comprising:

identifying a first connection in the knowledge graph, wherein the first connection represents a comparison between the first therapy and at least one other therapy in the plurality of therapies; and determining that the first connection was generated based at least in part on the first document;

determining a first criterion stated in the first document;

determining a first aggregate value for the first criterion, based on a plurality of participants associated with the first document, wherein the first aggregate value represents attributes of the plurality of participants;

generating a first weight for the first document, based at least in part on the first plurality of attributes and the first aggregate value;

generating a first score for the first therapy, based at least in part on the first weight; and determining an optimal therapy, from the plurality of therapies, based in part on the first score.

14. The system of claim 13, wherein determining the first aggregate value for the first criterion comprises:

identifying a first attribute that corresponds to the first criterion; and determining a distribution of values of the first attribute, with respect to the plurality of participants associated with the first document.

15. The system of claim 14, wherein determining the first weight for the first document comprises:

determining a first value of the first attribute based on the first profile;

determining a variance between the first value and the first aggregate value; and refining the first weight based on the variance.

16. The system of claim 13, wherein generating the first score for the first therapy comprises determining a revised strength for the first connection, based on a plurality of studies associated with the first connection.

17. The system of claim 13, wherein generating the first weight for the first document further comprises:

identifying a shared attribute that has a common value among the plurality of participants associated with the first document;

determining that the shared attribute is not included in a first plurality of criteria specified in the first document;

determining a first value of the shared attribute based on the first profile; and refining the first weight based on determining whether the first value matches the common value.

\* \* \* \* \*